United States Patent [19]

Smith, Jr. et al.

[11] Patent Number: 5,456,692
[45] Date of Patent: Oct. 10, 1995

[54] SYSTEM AND METHOD FOR NONINVASIVELY ALTERING THE FUNCTION OF AN IMPLANTED PACEMAKER

[75] Inventors: Robert E. Smith, Jr., Bradbury; Jeffery D. Snell, Northridge, both of Calif.

[73] Assignee: Pacesetter, Inc., Sylmar, Calif.

[21] Appl. No.: 116,423

[22] Filed: Sep. 3, 1993

[51] Int. Cl.$^6$ .................................................. A61N 1/37
[52] U.S. Cl. .............................................................. 607/31
[58] Field of Search ......................................... 607/30–31

[56] References Cited

U.S. PATENT DOCUMENTS

| | | | |
|---|---|---|---|
| 4,208,008 | 6/1980 | Smith | 607/31 |
| 4,304,238 | 12/1981 | Fischer | 607/31 |
| 4,401,120 | 8/1983 | Hartlaub et al. | 607/31 |
| 4,553,547 | 11/1985 | Keimel | 607/30 |
| 4,617,937 | 9/1986 | Batty, Jr. | 607/31 |
| 4,867,163 | 9/1989 | Schaldach | 607/30 |
| 4,979,507 | 12/1990 | Heinz et al. | 607/30 |
| 5,016,632 | 5/1991 | Hoegnelid et al. | 607/30 |
| 5,044,365 | 9/1991 | Webb et al. | 607/31 |
| 5,081,987 | 1/1992 | Nigam | 607/30 |

FOREIGN PATENT DOCUMENTS

| | | | |
|---|---|---|---|
| 0640002 | 11/1982 | European Pat. Off. | 607/31 |

Primary Examiner—William E. Kamm
Attorney, Agent, or Firm—Harold C. Schloss

[57] ABSTRACT

A system and method for safely altering the function of an implanted pacemaker in a noninvasive manner includes an implantable programmable pacemaker and a non-implantable programming device. The pacemaker includes a pulse generator that generates stimulation pulses as controlled by a control program. The control program, and associated control parameters, are stored in an implantable memory included within the pacemaker. The pacemaker further includes a telemetry circuit that allows the control parameters to be selectively changed or altered from a location remote from the pacemaker (i.e., a non-implanted location). The programmer includes a telemetry head for establishing a telemetry link with the pacemaker's telemetry circuit. Once a telemetry link is established, the programmer may be selectively operated to download a new control program into the pacemaker memory, thereby replacing the old control program previously stored in the pacemaker memory. As the downloading of the new control program takes place (which may require several minutes), the pacemaker includes backup control circuits, or equivalent, for controlling the pulse generator so that stimulation pulses are provided, as needed, until the downloading operation has been successfully completed. In this manner, the control program of the implantable pacemaker is noninvasively updated without having to explant the pacemaker, and without having to cease operation of the pacemaker.

30 Claims, 7 Drawing Sheets

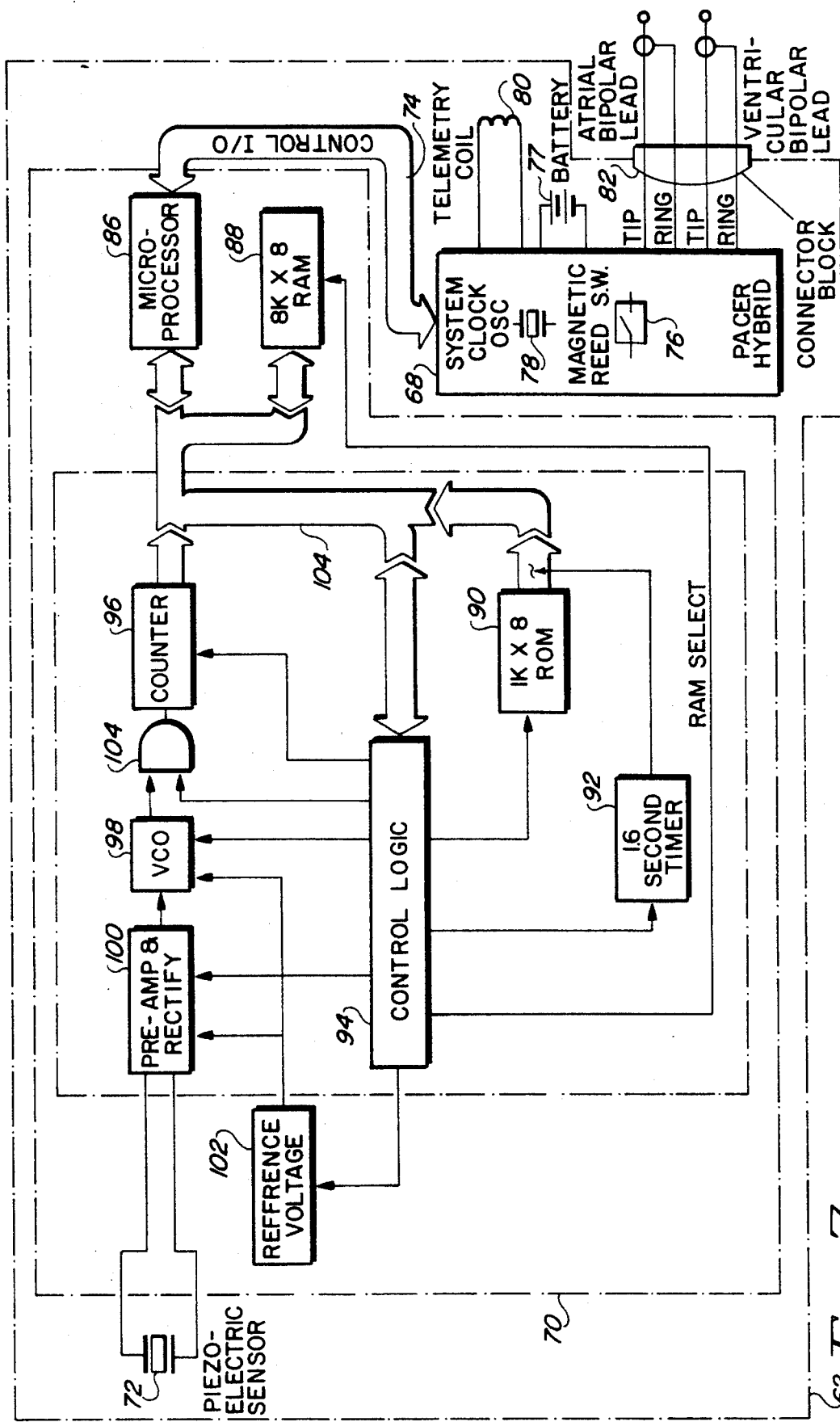

SYSTEM AND METHOD FOR NONINVASIVELY ALTERING THE FUNCTION OF AN IMPLANTED PACEMAKER

FIELD OF THE INVENTION

The present invention relates to implantable medical devices and methods, and more particularly, to a system and method for safely altering the function of an implanted pacemaker in a noninvasive manner. Even more particularly, the present invention relates to a pacing system that allows the pacing program stored in an implantable pacemaker to be updated, as required (e.g., to add new features or functions), using an external programmer that is in contact with the implantable pacemaker through a telemetry link. During the downloading time (which may take several minutes), the implantable pacemaker continues to provide its basic pacing function of assisting a patient's heart to beat, as needed, in a predetermined manner.

A pacemaker is an implantable medical device that delivers electrical stimulation pulses to a patient's heart, as required, in order to keep the heart beating at a desired rate. Early pacemakers provided stimulation pulses at a fixed rate or frequency, such as 70 pulses per minute (ppm), thereby maintaining the heartbeat at that fixed rate. Subsequently, pacemakers were designed to not only stimulate the heart, but also to monitor the heart. If a natural heartbeat was detected within a prescribed time period (usually referred to as the "escape interval"), no stimulation pulse was generated, thereby allowing the heart to beat on its own without consuming the limited power of the pacemaker. Such pacemakers are referred to as "demand pacemakers" because stimulation pulses are provided only as demanded by the heart.

Early demand pacemakers had a fixed base rate associated therewith. In later versions, the base rate was programmably selectable, and was commonly known as the "programmed rate." If the heart was able to beat on its own at a rate exceeding the base (or programmed) rate, then no stimulation pulses were generated. However, if the heart was not able to beat on its own at a rate exceeding the base rate, then stimulation pulses were provided to ensure that the heart would always beat at least at the base (or programmed) rate. Such operation was achieved by simply monitoring the heart for a natural beat during the escape interval. If a natural beat was sensed, the timer that defined the escape interval was reset. If no natural activity was sensed, a stimulation pulse was provided as soon as the escape interval timed out. Changing the base [or programmed] rate was accomplished by simply changing the duration of the escape interval.

Early demand pacemakers were single-chamber pacemakers that monitored and provided stimulation pulses to just one chamber of the heart, usually the right ventricle. More recent demand pacemakers have provided dual-chamber capability, i.e., the ability to sense and pace in both the right atrium and the right ventricle. With the ability to sense and pace in both chambers, the pacing circuitry used within the pacemaker has become increasingly more complex. No longer is it sufficient for a pacemaker, particularly a dual-chamber pacemaker, to simply generate stimulation pulses on demand. Rather, the pacemaker circuits must not only sense and distinguish an atrial contraction from a ventricular contraction, but they must also, for example, distinguish an atrial or ventricular contraction from noise, sense a premature ventricular contraction, a ventricular tachycardia or other cardiac arrhythmias, and respond to such sensed events in an appropriate manner.

Moreover, in recent years, rate-responsive pacemakers have been developed that automatically change the rate at which the pacemaker provides stimulation pulses (the "pacing rate") as a function of a sensed physiological parameter. The physiological parameter provides some indication of whether the heart should beat faster or slower, depending upon the physiological needs of the pacemaker user. Thus, for example, if a patient is at rest, there is generally no need for a faster-than-normal heart rate, so the rate-responsive pacemaker maintains the "base rate" at a normal value, such as 60 ppm. However, if the patent is exercising, or otherwise physiologically active, there is a need for the heart to beat much faster, such as 100 beats per minute. For some patients, the heart is not able to beat faster on its own, so the pacemaker must provide assistance. In order to do this effectively, the physiological need for the heart to beat faster must first be sensed, and the "base rate" of the rate-responsive pacer must be adjusted accordingly. Hence, rate-responsive pacemakers are known in the art that increase and decrease the "base rate" as a function of sensed physiological need. (Note, as used herein, the term "pacing rate" refers to the rate at which the pacer provides stimulation pulses, or in the case of demand pacers, the rate at which the pacer would provide stimulation pulses in the absence of naturally occurring heartbeats. Also, for purposes of this application, the terms "pacer" and "pacemaker" are used interchangeably.)

Numerous types of sensors are used by rate-responsive pacemakers in the prior art in an attempt to sense the patient's true physiological need. Unfortunately, no one sensor is known that accurately senses a single parameter that consistently provides an indication of the patient's true physiological need. Hence, multiple sensors may be used, with the signals generated by each sensor being combined in an appropriate manner to provide a composite sensor signal that best indicates the patient's true physiological need.

The addition of rate-responsive features and multiple-sensor processing capabilities further adds to the complexity of the pacing circuits required by today's implantable pacemaker. In order to efficiently handle such increased complexity during the design, manufacture, and operation of a pacemaker, it is known in the art to use a control processor within the pacemaker to control the operation of the pacemaker in a prescribed manner. Such control processor is, in effect, a small computer (e.g., a microprocessor) that executes a specific sequence of commands or instructions as dictated by a "control program" (sometimes referred to as an "operating program"), and by a set of control parameters. The control program is permanently stored within the pacemaker in a non-erasable read only memory (ROM) or equivalent non-volatile memory storage device. The control parameters, on the other hand, are stored in a random access memory (RAM), and may be programmably altered from time to time in order to allow the pacemaker to meet the needs of a particular patient. The control parameters define, for example, the pacing rate, the pacemaker sensitivity, the amplitude of the pacing stimulus, the pacing mode of the pacemaker, and similar control variables that, in combination with the control program stored in the pacer ROM, define and control the operation of the pacemaker.

The control parameters are supplemented for certain types of pacemakers, as programmed, by sensed control variables, such as one or more sensed physiological parameters, that give an indication of how the pacing rate should change in order to best meet the physiological demands placed on the patient. Advantageously, being able to program the control parameters adds needed flexibility to the operation of the pacemaker so that the basic control program can be customized to best meet the needs of a particular patient at a particular time. Further, by sensing appropriate control variables, the operation of the pacemaker may adaptively change to follow the changing demands of the patient.

Disadvantageously, even though a great deal of flexibility and adaptability can be achieved in the operation of a pacemaker by selectively changing the control parameters and by sensing appropriate control variables, the basic control program itself is fixed. It is fixed because it is permanently stored, or otherwise incorporated into the design, of the pacemaker circuits. Such permanence provides a measure of safety for the patient because no matter what values the control parameters and variables may assume, the pacer will still be forced to provide the basic output for which it was designed, e.g., pacing pulses on demand. However, such permanence may also be severely limiting because it prevents the patient from taking advantage of improvements that could otherwise be made in the control program, e.g., to process the signal(s) from a physiological sensor in an improved manner, or to update the sensor processing portion of the control program to accommodate a new type of sensor.

Heretofore, whenever there has been a need for a new or upgraded control program, it has been necessary to introduce a new model of pacemaker that includes such new or upgraded control program. Unfortunately, a patient who already has an implanted pacemaker cannot take advantage of such improvement or upgrade without explanting his or her existing pacemaker, and implanting the new pacemaker. Such explant/implant procedure is not only expensive, but may also pose a health risk to the patient. What is needed, therefore, is an implantable pacemaker that allows its control program to be safely and noninvasively altered without compromising the safety of the patient.

It is known in the art to provide an implantable pacemaker wherein a plurality of control programs are stored in the pacemaker, and a control parameter is programmed to select which of the control programs is used at a given time to control the operation of the pacemaker. See, e.g., U.S. Pat. No. 4,958,362, issued to Duggan. Disadvantageously, such multiple control program scheme requires additional memory capacity. Such additional memory capacity either increases the size and cost of the pacemaker, or monopolizes available memory capacity that could be better used for other purposes. Moreover, such multiple control program scheme still does not allow a basic improvement or new program to be safely added to the pacemaker after its manufacture and implant. What is thus needed is a way for safely downloading a new control program to a pacemaker that has already been implanted in a patient.

SUMMARY OF THE INVENTION

The present invention addresses the above and other needs by providing a system and method that allows the control program of an implantable pacemaker to be noninvasively updated. Such a system includes an implantable programmable pacemaker, and a non-implantable programming device. The pacemaker includes a pulse generator that generates stimulation pulses as controlled by a control program. The control program, and associated control parameters, are stored in a memory element included within the pacemaker. The pacemaker further includes a telemetry circuit (or equivalent communications channel) that allows the control program and associated control parameters to be selectively changed or altered from a non-implanted location external to the pacemaker. The programmer has a telemetry head (or equivalent communication circuitry) for establishing a telemetry link with the pacemaker's telemetry circuit. Once a telemetry link is established between the implanted pacemaker and the non-implanted programmer, the programmer may be selectively operated so as to download a new control program into the pacemaker memory, thereby replacing the old control program previously stored in the pacemaker memory. Advantageously, as the downloading of the new control program takes place (which may require several minutes), the pacemaker includes backup means for controlling the pulse generator so that stimulation pulses continue to be provided to the patient, as needed, until the downloading operation has been successfully completed. Thus, in this manner, the control program of the implantable pacemaker may be noninvasively updated without having to explant the pacemaker, and without having to stop the operation of the pacemaker during the downloading process.

The backup means of the pacemaker that controls the pulse generator during the downloading process may take several forms. In accordance with one aspect of the invention, the pacemaker includes a separate pulse generator circuit or chip that is capable of operating independently from the control program. In accordance with another aspect of the invention, the control program includes at least two portions, with a first portion controlling the operation of the pulse generator, and a second portion controlling a function that supplements the pulse generator function, e.g., the processing of a raw sensor signal in order to arrive at a sensor-indicated pacing rate. The new control program that is downloaded to the pacemaker replaces only the second portion, leaving the first portion unmodified and available to control the pulse generator during the downloading process.

In accordance with yet another aspect of the invention, a first portion of the control program is copied into a temporary memory location, apart from the main memory location where the control program normally resides. During the downloading process, the pulse generator looks to the temporary memory for its control, while the main memory location is updated with the new control program.

One embodiment of the invention may be characterized as a method for noninvasively altering the function of an implantable pacemaker. Such a pacemaker, like all pacemakers, includes pulse generator means for providing stimulation pulses on demand in accordance with a basic operating mode. The pacemaker also includes means for conditioning the operation of the pacemaker in accordance with a first control program stored in a memory device or element located within the implantable pacemaker. Such first control program defines at least one of the functions carried out by the implantable pacemaker, e.g., the rate-responsive functions. The method includes, as a first step, establishing a telemetry link between the implantable pacemaker and an external programmer through which selected control parameters associated with the first control program may be selectively changed. Thus, the functions carried out by the pacemaker may be selectively programmed to operate in a prescribed manner, as is commonly done with any programmable implantable pacemaker of the prior art. Unlike programmable implantable pacemakers of the prior art, however, a second step of the method includes downloading a second control program from the external programmer to the memory of the implantable pacemaker through the established telemetry link. Such second control program is stored in the pacemaker memory so as to replace the first control program. In this manner, at least one of the functions carried out by the pacemaker may be noninvasively altered.

An important aspect of the above-described method is that the downloading of the second control program occurs in such a way that the pulse generator continues its basic operating mode even during the downloading process. In this way, the first control program may be upgraded, i.e., replaced with a later version, without having to interrupt the pacemaker's basic operation.

In accordance with another embodiment, the invention may be characterized as a pacing system. Such pacing system includes two main components: an implantable pacemaker and an external programmer. The implantable pacemaker has means for generating stimulation pulses and delivering such stimulation pulses to a patient's heart in accordance with a prescribed mode of operation. The prescribed mode of operation is dependent, at least in part, on a control program stored in the pacemaker's memory. The external programmer has means for establishing a telemetry link with the implantable pacemaker. Significantly, the external programmer also includes reprogramming means for noninvasively altering the control program stored in the pacemaker's memory through the established telemetry link. In a preferred embodiment, the entire control program stored in the pacemaker's memory may be completely replaced with a new control program without interrupting the basic mode of operation of the pulse generator. Thus, the pacing system provides a safe means for upgrading or modifying the pacemaker's functions without having to explant and replace the pacemaker.

It is thus a feature of the invention to provide a pacing system and method that allows at least one of the functions carried out by an implantable pacemaker to be noninvasively altered or updated from a non-implanted location remote from the implantable pacemaker.

It is another feature of the invention to provide such a pacing system and method that allows a new control program to be downloaded to the memory circuits of an implantable pacemaker at the same time that the pacemaker continues to carry out its basic pacing function.

It is yet a further feature of the invention to provide an implantable pacemaker that includes at least two independent processing circuits, or equivalent, to respectively control the basic pacing function and a supplemental pacing function as controlled by respective control programs; and wherein the controlling program of at least one of the processing circuits can be noninvasely updated or replaced, as required, after implantation of the pacemaker.

BRIEF DESCRIPTION OF THE DRAWINGS

The above and other aspects, features and advantages of the present invention will be more apparent from the following Detailed Description of the Invention presented in conjunction with the following drawings, wherein:

FIG. 7 is a block diagram of a preferred embodiment of the rate-responsive pacemaker for the pacing system shown in FIG. 6;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
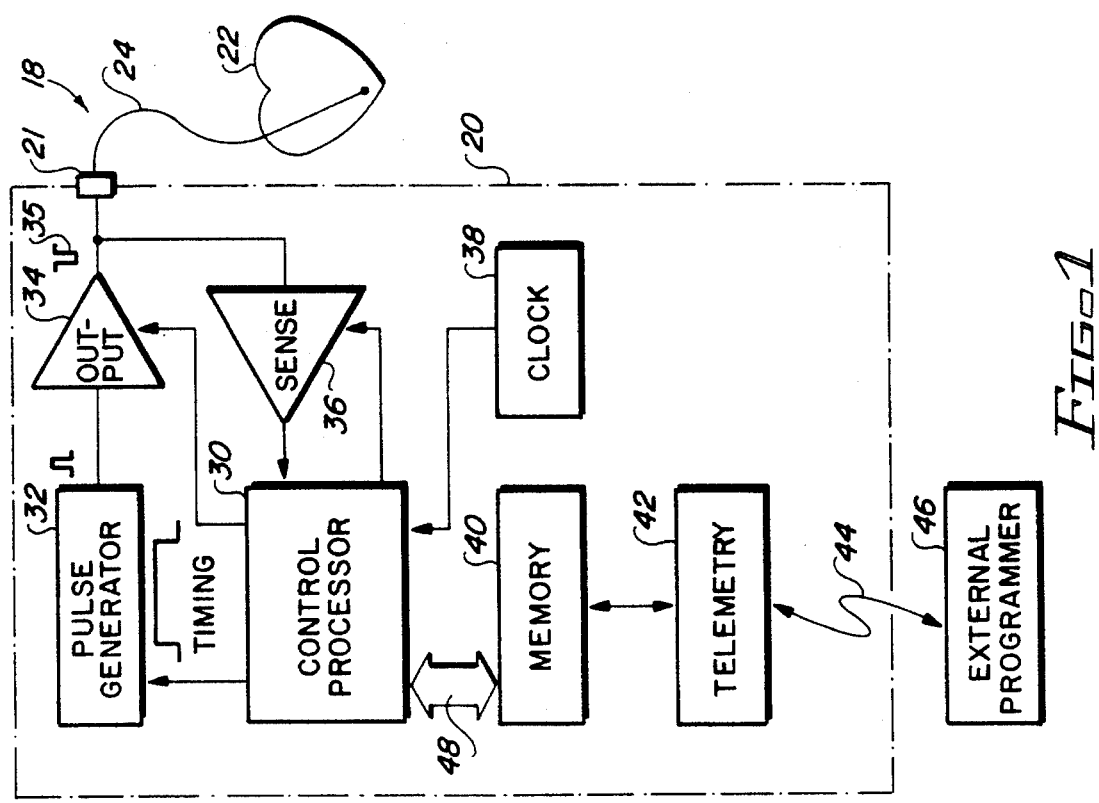
FIG. 1 shows a block diagram of a first embodiment of a pacing system made in accordance with the present invention.

Referring first to FIG. 1, there is shown a functional block diagram of a first embodiment of a pacing system 18 made in accordance with the present invention. The pacing system includes an implantable pacemaker 20 and an external programmer 46. The pacemaker 20 includes an output connector 21 through which a pacing lead 24 may be connected to the internal circuits of the pacemaker. The lead 24 is typically an endocardial lead that is adapted for insertion into a selected chamber of a heart 22. FIG. 1 shows a single lead 24 being used to contact a single-chamber of the heart 22. However, it is to be understood that the use of a single lead in this manner is only exemplary, as the invention may be used equally well with pacing systems that include multiple leads that make contact with multiple locations within the patient's heart, or other body tissue locations.

The internal circuits of the pacemaker with which the pacing lead 24 makes contact when inserted into the connector 21 include an output amplifier 34 and a sense amplifier 36. The output amplifier 34 generates an electrical stimulation pulse 35 as controlled by a pulse generator 32. The pulse generator 32, in turn, receives timing signals from a control processor 30. Such timing signals control when, within a given cardiac cycle, the stimulation pulses 35 are to be generated. (As is known in the art, a "cardiac cycle" comprises the period of time it takes the heart to complete one heartbeat. Such cardiac cycle time period, which typically may vary for a patient at rest anywhere from 800 to 1000 msec [corresponding to a heart rate of from 75 to 60 beats per minute (bpm)], includes an atrial tissue depolarization [manifest by the occurrence of a "P-wave"], signaling contraction of the atrial cardiac tissue; followed by a ventricular tissue depolarization [manifest by the occurrence of an "R-wave"], signaling contraction of the ventricular cardiac tissue.)

The sense amplifier 36 monitors the electrical signals appearing on the lead 24, and processes such signals to determine whether they are indicative of an atrial and/or ventricular depolarization. Such processing typically includes amplification, filtering, and threshold detection. If a valid depolarization signal ("cardiac event") is sensed by the sense amplifier 36, i.e., if the sense amplifier senses an R-wave and/or a P-wave, then the sense amplifier provides an appropriate signal to the control processor 30 of such sensed cardiac event. If no valid cardiac events are sensed during a prescribed time period, referred to generally as the "escape interval," i.e., if no R-wave is sensed for ventricular sensing (or no P-wave is sensed for atrial sensing), then the control processor 30 signals the pulse generator to generate a stimulation pulse. If a valid cardiac event is sensed before the escape interval times out, the control processor responds by resetting the escape interval, thereby preventing the pulse generator from generating a stimulation pulse. In this manner, the pacemaker 20 provides stimulation pulses only when needed, e.g., only when a valid cardiac event is not sensed.

A clock circuit 38 provides the necessary clock signals for operation of the control processor 30. The control processor 30, which may be a microprocessor or equivalent processing circuit, operates in accordance with a control program that is stored in the pacemaker memory 40. Also stored in the memory 40 is a set of control parameters that are used by the control program as it defines the operation of the processor 30. That is, the control parameters define the various variables associated with the operation of the pacemaker, such as the duration of the escape interval, the amplitude of the stimulation pulse, the width of the stimulation pulse, and the like. The control program specifies the particular order or sequence of events that are carried out by the processor 30. For example, the control program may specify that, upon detecting a valid atrial event, a control parameter stored in a particular address in the memory 40 should be retrieved in order to define an appropriate atrial-to-ventricular (AV) delay. The control program may further specify that if a valid ventricular event is sensed before the AV delay times out, then another control parameter stored in another location (address) of the memory 40 should be retrieved in order to define an appropriate ventricular-to-atrial (VA) delay. If a valid ventricular event is not sensed before the timing out of the AV delay, then the control program may specify another memory address where a control parameter is stored that defines the amplitude and pulse width of a stimulation pulse that is to be generated.

Of course, the above example is extremely simple, but it illustrates the basic operation of the pacemaker 20. Those skilled in the art will recognize that there are numerous events associated with a cardiac cycle, and that there are numerous types of cardiac cycles that may occur. See, e.g., U.S. Pat. Nos. 4,712,555 and 4,940,052, both of which are incorporated herein by reference, and each of which describes the operation of a particular type of implantable pacemaker (a "rate-responsive" pacemaker) in much greater detail. The control program, in combination with the other control circuitry within the pacemaker, thus define how the pacemaker responds to each possible event and cardiac cycle type. The control parameters, in turn, define the magnitude of the variables associated with such response, e.g., the duration of time periods, the amplitude and widths of stimulation pulses, the gain of amplifiers, the threshold level of threshold detectors, and the like.

In order to add flexibility to the operation of the pacemaker 20, the pacemaker also includes a telemetry circuit 42. The telemetry circuit 42 allows access to the memory 40 from a remote location, e.g., from an external programmer 46 at a non-implanted location. The external programmer 46 includes means for establishing a telemetry link 44 with the telemetry circuit 42 of the implanted pacemaker. Through this telemetry link 44, control parameters may be sent to the telemetry circuit 42 for storage in the memory 40. Such control parameters may thereafter be used by the control program stored in the memory 40 to steer the operation of the pacemaker 20, as explained above. Additional details associated with the design and operation of a telemetry circuit 42, as well as an external programmer 46, may be found in U.S. Pat. Nos. 4,809,697 and 4,944,299, which patents are incorporated herein by reference.

In operation, the external programmer 46 is used to programmably set the control parameters associated with operation of the control processor 30. However, heretofore, the external programmer 46 has not ever been used to alter or change the control program once the pacemaker has been implanted in a patient. Rather, the control program is downloaded to the memory 40 during the manufacture of the pacemaker 20. In some instances, the control program is stored in read only memory (ROM), or equivalent hard-wired circuitry, so that it can never to updated or changed thereafter. In other instances, it is stored in random access memory (RAM), but access to it is denied. This is done purposefully to preserve the integrity of the control program, or stated more accurately, to preserve the integrity of the function(s) controlled by the control program. That is, in the interest of the patient's safety, it generally has not been considered appropriate to download a new control program in an implantable medical after such device has been implanted. To this end, implantable medical devices (including pacemakers, and the external programmers used with such pacemakers) are strictly regulated by appropriate governmental agencies, such as (in the United States) the Federal Drug Administration (FDA). The FDA, for example, must not only initially approve an implantable pacemaker before it can be used on a commercial basis by the medical community, but must also approve any modification subsequently made to the devices, or to any electronic circuitry that interfaces with the devices. Hence, heretofore it has not been possible to download a new control program to a pacemaker because such new control program would have to first be approved by the FDA, and such approval may take months or years to obtain. Thus, pacemaker manufacturers have heretofore fixed the control programs of their implantable pacemakers at the time of manufacture so that they cannot be changed. If they (the control programs) need to be changed, e.g., to add new features or capabilities, then a new model pacemaker has been introduced that incorporates the changed control program, which new model pacemaker must then go through the rigorous FDA (or other governmental agency) approval cycle.

In contrast to the control program, which has heretofore been fixed, certain control parameters that define the variables used by the control program (or equivalent circuitry) in controlling the pacemaker are readily changed, from time to time, after implantation by using the external programmer 46. Thus, should there be a need to change a given control parameter, e.g., the stimulation pulse amplitude generated by the output amplifier 34, the sensitivity (threshold setting) of the sense amplifier 36, or other variables, then the appropriate control parameters that define such variables are simply updated (programmed) through the telemetry link established by the external programmer 46. However, such programming of the control parameters is limited so that the associated variables can only be changed within certain safe limits that are defined by the control program and/or other circuitry within the pacemaker.

In accordance with the embodiment of the invention depicted in FIG. 1, the memory 40 is a RAM memory that has both a control program and a set of control parameters stored therein at respective memory locations (addresses). Like conventional programmable pacemakers, the set of control parameters in the memory 40 may be selectively updated (programmed), as needed, through use of the external programmer 46. Unlike conventional programmable pacemakers, the control program stored in the memory 40 may also be updated, using appropriate safeguards, through use of the external programmer 46. Thus, when new features requiring a new control program are added to the pacemaker, a patient having an existing implanted pacemaker can receive the benefits of such new features by simply upgrading the control program stored in his or her implanted pacemaker. In this manner, the invention allows an existing control program stored in an implanted pacemaker to be noninvasively upgraded to a new version of the control program.

Several safeguards are utilized to ensure the safe transfer of the new control program to the pacemaker memory. First, the program must be downloaded from an approved programming device. Note, the term "downloaded" or "downloading," as used herein, refers to the transfer of a control program from an external programmer to an implanted medical device. By "approved," it is meant that the programming device has been approved by the FDA, or other applicable governmental agency. Second, the programmer is configured so that only approved control programs are allowed to be downloaded. Third, only authorized, trained personnel are allowed to use the programmer in a downloading mode. Hence, not every person, e.g., not every physician who has a programmer 46, has the ability or knowledge to use the programmer in a downloading mode. Rather, downloading of a new control program will typically only take place by specially trained field clinical engineers (who do have the knowledge, e.g., special passwords, of how to perform the downloading operation) working in conjunction with, or under the direction of, the patient's physician (who has the knowledge of which new control program would be best suited for the patient).

Figure 2:
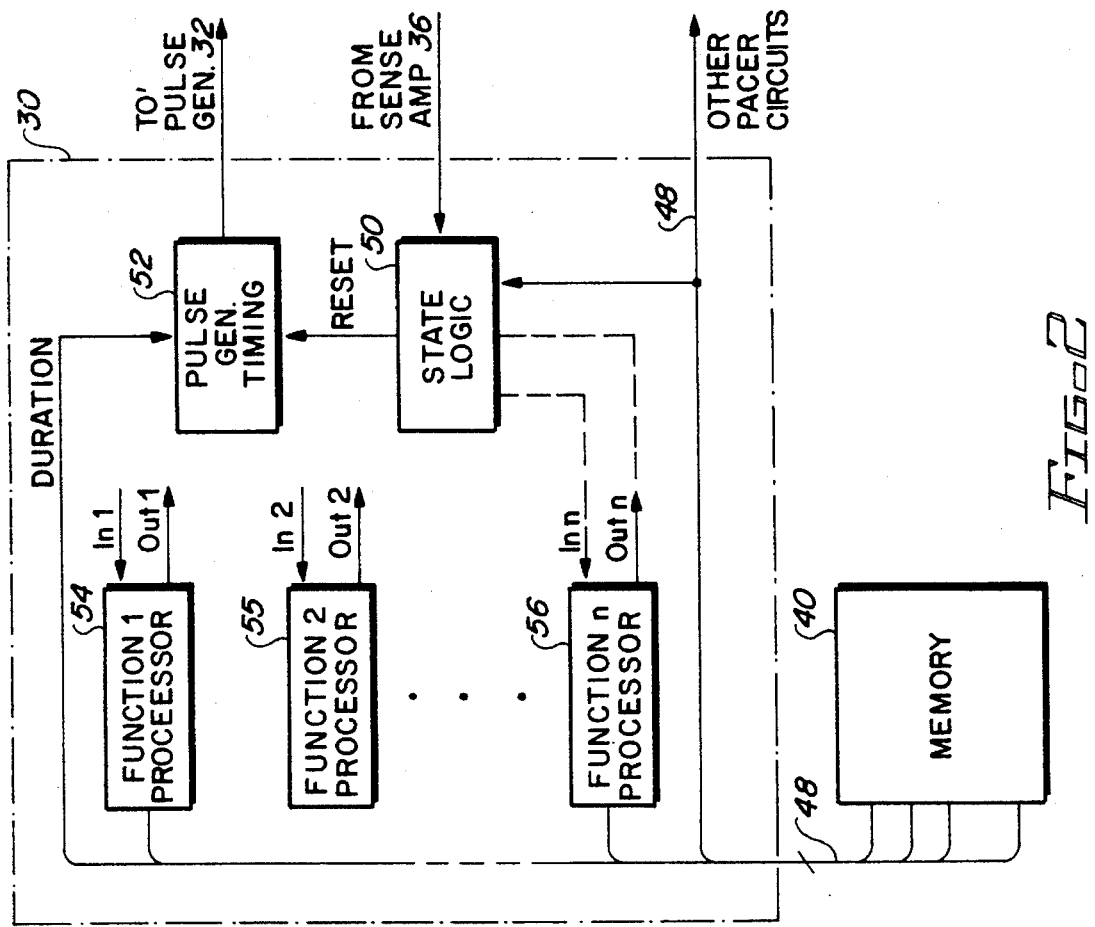
FIG. 2 is a block diagram of one embodiment of the control processor of FIG. 1.

Further, in accordance with the embodiment of the invention shown in FIG. 1, the control processor 30 may include multiple processors 54, 55 and 56, as illustrated in FIG. 2. Each processor 54, 55 and 56 is programmed, using a respective control program stored in the memory 40, to perform a specific function associated with the operation of the pacemaker 20. Such functions are supplemental to the main pacemaker function, which is to monitor the heart 22 for natural cardiac events, and to provide stimulation pulses in the event that no natural cardiac events are sensed, in accordance with a prescribed pacer mode.

As seen in FIG. 2, which shows one embodiment of the control processor 30 of FIG. 1, the main pacemaker function, as well as the prescribed pacer mode, are carried out by appropriate state logic circuitry 50, which state logic circuitry 50 may be considered as a dedicated control circuit for the pacemaker 20. The use of state logic in the control of an implantable pacemaker is described, e.g., in the '555 patent, previously referenced.

The state logic 50 defines the state of the pacemaker as a function of the input signals it receives. One such input is from the sense amplifier 36 (which may include inputs from both atrial and ventricular channels, depending upon the particular pacemaker configuration that is used). Another set of inputs to the state logic is a set of control parameters obtained from the memory 40 over a data bus 48. The data bus 48 interfaces the memory 40 with the various circuits used within the pacemaker. Thus, for example, a set of control parameters defines a particular operating mode for the state logic. Such operating mode dictates the particular sequence followed by the state logic, e.g., whether it operates in a VVI mode, or a DDD mode, as it carries out the basic pacing function. (The three letter code used to indicate the various pacer modes is standardized in the industry. See, e.g., the '555 patent at col. 10, line 52 to col. 11, line 6. Another set of control parameters defines the duration of the timing interval used by pulse generator (PG) timing circuitry 52 in controlling the various time intervals, e.g., escape intervals, used by the pacemaker as it carries out its pacing basic function.

Still other of the control parameters available on the data bus 48 are directed to the appropriate circuits that use such parameters in controlling the operation of the pacemaker, e.g., the sensitivity control parameter is directed to the sense amplifier 36; the pulse amplitude and width control parameters are directed to the output amplifier 34; and so on.

The functions carried out by each of the processors 54, 55 and 56 may be varied, depending upon the particular needs of the patient. (It is to be understood that just because three processors 54, 55 and 56 are shown in FIG. 2 as part of the control processor 30, the invention is not so limited. The control processor 30, for the particular embodiment shown in FIG. 2, may include any number of processors, e.g., 1 to 10, that supplement the basic pacing function carried out by the state logic 50. The functions carried out by the processors 54, 55 and/or 56 may include, e.g., the sensing and processing of a physiological parameter, such as physical activity, blood oxygen saturation, blood pressure, respiration rate, PR interval, etc. Further, the processors may monitor and report parameters associated with the operation of the pacemaker, such as remaining battery life, the time of day, the occurrences of prescribed events (such as premature ventricular contractions, event histogram data, etc.), and the like. Indeed, the processors 54, 55, 56 . . . (however many may be used) may be used for many different types and varied functions associated with the use and operation of an implantable pacemaker.

As seen in FIG. 2, the control processor 30 is effectively divided into two portions: (1) a portion that controls the basic pacing functions, comprising the state logic 50 and the pulse generator (PG) timing circuits 52; and (2) a portion that controls the supplemental pacing functions, comprising the processors 54, 55, and/or 56. It is to be understood that the first control processor portion, i.e., the portion that controls the basic pacing function, could be realized using circuitry other than that shown in FIG. 2. For example, a suitable processor circuit, such as a microprocessor circuit, could readily be programmed to perform the basic pacing function carried out by the state logic 50 and PG timing circuitry 52. Similarly, the functions carried out by the supplemental processors 54, 55 and/or 56 could likewise be achieved using specially designed hardware circuits. Indeed, any configuration of the control processor 30 that provides both supplemental and basic pacing functions could be utilized, whether such configuration uses conventional processing circuits (e.g., microprocessors) or dedicated logic circuitry (e.g., state logic).

One of the advantages of having the control processor 30 configured as shown in FIG. 2 (to provide both the basic pacing function and supplemental pacing functions) is that the control programs for the supplemental pacing function(s) can be altered (upgraded with a new program) at the same time that the basic pacing function continues to operate. Thus, there need be no interruption in the basic pacing function provided by the pacemaker as one or more control programs are downloaded to the memory 40. As the downloading operation could take several minutes, this is an important advantage because it means the patient need not go without the potentially life-sustaining stimulation pulses provided by the pacemaker.

Figure 3:
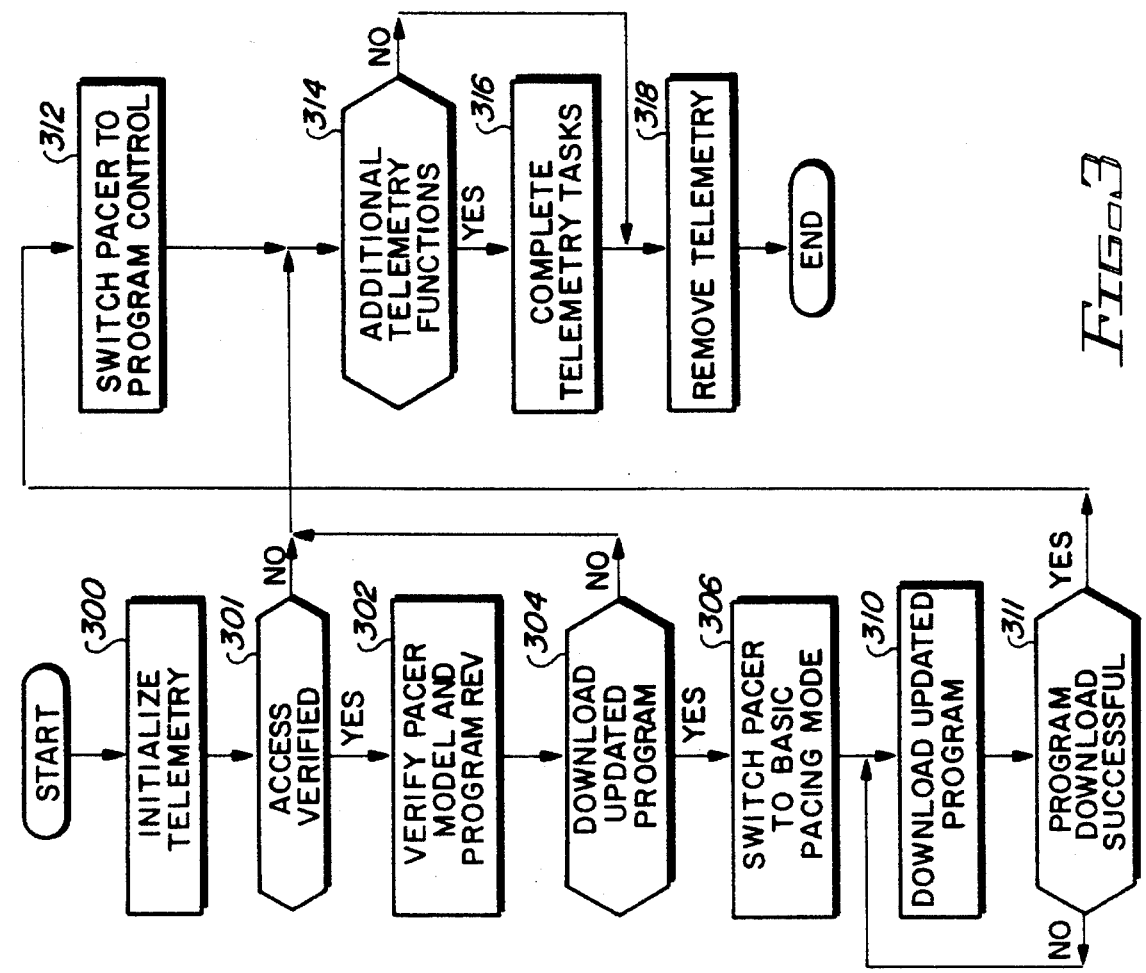
FIG. 3 is a simplified flowchart that depicts the basic process used to download a new control program to the memory of the pacemaker of FIG. 1.

Turning next to FIG. 3, a simplified flowchart depicting the basic process used to download a new control program to the memory 40 of the pacemaker 20 is illustrated. In this and other flowcharts presented herein, each main step of the process is depicted as a "box" or "block," with each box or block having a reference number assigned thereto. Rectangular-shaped blocks refer to a particular step that is carried out. Diamond-shaped blocks refer to a particular decision or determination (i.e., a "test") that is made, with the outcome being either "yes" or "no." It is submitted that those of skill in the programming arts, given the information presented herein, could readily fashion the appropriate "code" (i.e., control program) that carries out the steps indicated in the flowchart of FIG. 3 for whatever type of processing circuit, or equivalent, that may be used.

As seen in FIG. 3, a first step of the downloading process is to "initialize telemetry" (block 300), which means that a telemetry link must be established between the implantable pacemaker and an external programmer. Typically, such link is established by placing a telemetry head coupled to the external programmer over the general area where the pacemaker is implanted, and activating the appropriate commands on the external programmer that open up such telemetry link. See, e.g., U.S. Pat. Nos. 4,809,697 and 4,944,299, previously cited. Once such telemetry link has been established, a next step determines whether access to the control program is to be granted (block 301). Access verification is typically achieved by means of a password, or a series of passwords, that are known only to field clinical engineers, or others, who are authorized and have sufficient training to be able to replace the control program.

If access verification is denied ("no" branch of block 301), i.e., if the proper password(s) are not given, then access to the downloading process is not granted, and a determination is made as to whether there are any additional telemetry functions that need to be performed (block 314). If so, then such other telemetry functions are addressed and completed in conventional manner (block 316). Such other telemetry functions may include, e.g., programming new control parameters, monitoring the status of the pacemaker, and the like. If not, then the telemetry link established with the pacemaker may be removed and the process is completed (block 318). The telemetry link is normally removed by simply removing the telemetry head and, as appropriate, turning off the external programmer.

If access verification is granted ("yes" branch from block 301), then the first step to modifying the control program is to check the existing control program to make sure it is one that needs to be modified (block 302). Typically, this is done by retrieving data from the pacemaker memory that indicates the model of the pacemaker, as well as the version (e.g., revision level) of the control program that is stored therein. Such data, once retrieved, is displayed on a display screen of the external programmer.

Based on the pacemaker model and control program revision level data that is retrieved from the pacemaker, a determination is next made as to whether a new control program should be downloaded to the pacemaker (block 304). Such determination may be incorporated automatically into the downloading process by the external programmer, e.g., Rev. A of the control program is always replaced by Rev. B, Rev. B by Rev. C, and so on; or the determination can be made, or replacement of the control program can be confirmed, manually by the operator of the external programmer.

If a determination is made that the control program is not to be replaced ("no" branch of block 304), then the opportunity to make additional telemetry functions is performed as described above (blocks 314, 316 and 318) before the process is terminated.

If a determination is made that the control program is to be replaced ("yes" branch of block 304), then an appropriate command is automatically sent by the external programmer that causes the pacemaker to switch to a basic pacing mode (block 306). Such basic pacing mode assures that the pacemaker provides stimulation pulses on demand, or as otherwise programmed (e.g., at a constant rate) during the downloading process. Such step is necessary due to the length of time that may be required to complete the downloading process. For example, depending upon the size (number of bytes) included in the control program, the data transfer rate, and other factors, it may take up to several minutes, e.g., 15 minutes, to accurately download a complete control program to the memory of the implanted pacemaker. Such download time may be too long for the patient to go without receiving the benefits of an implanted pacemaker. Hence, it is crucial that some sort of backup pacing be provided during the downloading process.

Once the pacemaker has switched to its basic operating mode, the new (updated) control program is downloaded from the external programmer to the memory of the pacemaker (block 310). After downloading the new control program, the external programmer tests the program that was downloaded to make sure that it was downloaded accurately (block 311). If it wasn't, then the downloading of the control program is repeated (block 310). If it was, then the external programmer sends another command that causes the pacemaker to switch from its basic pacing mode to whatever mode or modes are controlled by the new control program (block 312). After switching the pacemaker back to control under the new control program, then the opportunity to make additional telemetry functions is performed as described above (blocks 314, 316 and 318) before the process is terminated.

Advantageously, any of the many and varied techniques commonly used in the data processing art to download a control program from one device to another may be used to download the new control program to the computer (block 310). For example, the downloading of the new control program may be performed by breaking the control program into respective smaller components, or blocks, with each block containing a prescribed number of bytes, or the code to perform a prescribed function. Then, the downloading process continues by: downloading a first block; verifying that the first block has been downloaded successfully; downloading a second block; verifying that the second block has been downloaded successfully; and so on, until all the blocks of the new control program have been downloaded.

Figure 4:
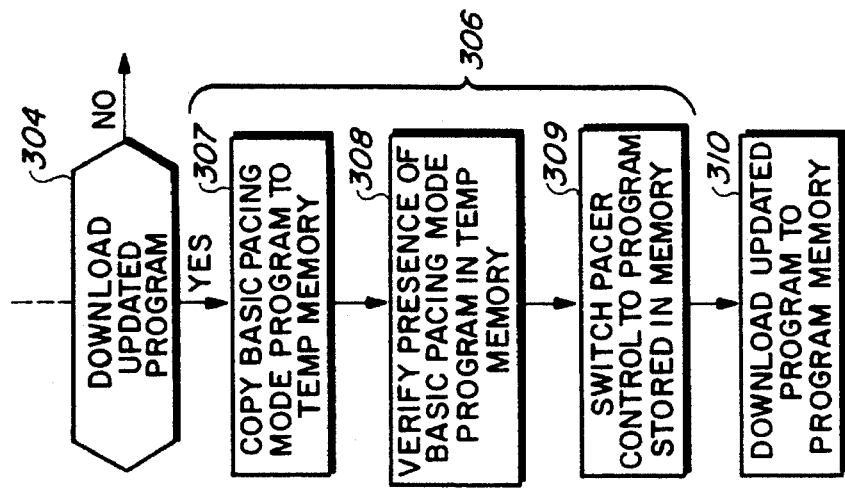
FIG. 4 is a more detailed flowchart that illustrates one step of the process shown in FIG. 3, i.e., the step of switching the pacer to its basic operating mode.

One technique that may be used to switch the pacer to its basic operating mode in anticipation of downloading a new control program (block 306) is further illustrated in FIG. 4. As seen in FIG. 4, a basic pacing mode control program, which is stored at a specified address in the pacemaker memory, is copied to a temporary memory location (block 307). The temporary memory location is selected to be a memory location that is not affected by the downloading of the new control program, and is thus "safe" during the downloading process. After copying the basic pacing mode program to temporary memory, it is checked to make sure that it has been successfully copied to the temporary memory (block 308). Once it has been verified that the basic pacing mode program has been successfully copied into the temporary memory, the control of the pacer is switched from the normal control program to the control program stored in the temporary memory (block 309). Thereafter, the new control program is downloaded to the pacer memory while the pacer operates as controlled by the basic mode pacing program stored in the temporary memory (block 310).

Another technique for switching the pacer to its basic operating mode is to utilize a mode switchable pacemaker that can perform one or more modes of operation without relying on a control program. If such a mode switchable pacemaker is employed, then the switching step (e.g., block 306 of FIG. 3) simply involves changing the mode of the pacemaker to an appropriate non-control-program mode. For example, if the pacemaker is a rate-responsive pacemaker that utilizes a physiological sensor in order to determine a sensor-indicated rate at which pacing stimuli are to be generated in the absence of natural cardiac events, and if the control program of such rate-responsive pacemaker specifies the manner in which the raw signal from the sensor is processed in order to arrive at the sensor-indicated rate, then the switching step of block 306 may simply involve switching the pacer to, e.g., a VVI mode (a non rate-responsive mode which does not rely on the rate-responsive control program) in lieu of a DDDR mode (a rate-responsive mode that does rely on the control program). An example of such a pacemaker is described more fully below in conjunction with FIGS. 6 through 10.

Figure 5:
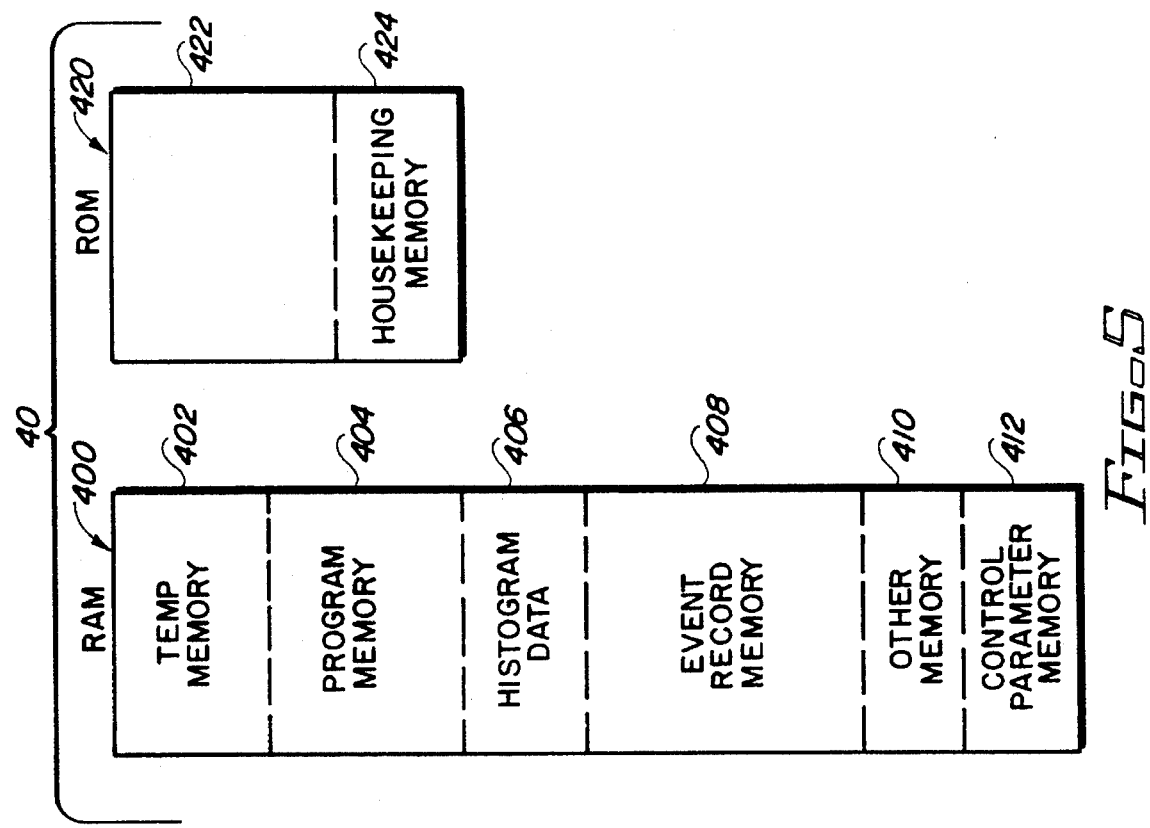
FIG. 5 depicts the organization of the memory of the pacemaker shown in FIG. 1.

FIG. 5 illustrates a representative organization of the memory 40 of the pacemaker 20 shown in FIGS. 1 and 2. Such memory 40 comprises a RAM component 400 and a ROM component 420. The ROM 420 includes at least a basic operating system portion 422 and a housekeeping portion 424. The operating system 422 has a basic operating system permanently written therein that allows fundamental operations needed to load program or other data into specified address locations of the RAM memory 400 to be carried out. The housekeeping portion 424 has a basic retrieval program permanently stored therein that allows specified address locations of the RAM 400 to be downloaded to the external programmer, and/or that allows certain housekeeping functions of the pacemaker to be carried out. Such housekeeping functions may include, for example, monitoring the battery impedance, monitoring the lead impedance, or even forcing the pacemaker to operate in a fail-safe mode under certain sensed conditions. The fail-safe mode may provide, e.g., generating stimulation pulses at a fixed rate, e.g. 70 ppm. For some embodiments, such a fail-safe mode may also function as the basic operating mode used while downloading a new control program (see block 306 of FIG. 3).

The RAM memory 400, for the configuration illustrated in FIG. 5, includes a temporary memory portion 402, a program memory portion 404, a histogram data portion 406, an event record portion 408, a spare portion 410 (wherein any other data or programs may be stored), and a control parameter portion 412. It is to be emphasized that the configuration shown in FIG. 5 for the RAM 400 is only exemplary, as any desired configuration may be used. For operation of the pacemaker 20, at least the program memory portion 404 and the control parameter portion 412 are needed. The other memory portions are optional, but if used, provide significant improvements or enhancements to the pacer operation. The use of histogram data and event record data are described, e.g., in U.S. Pat. No. 5,309,919, granted May 10, 1994, entitled METHOD AND SYSTEM FOR RECORDING, REPORTING, AND DISPLAYING THE DISTRIBUTION OF PACING EVENTS OVER TIME AND FOR USING SAME TO OPTIMIZE PROGRAMMING, which patent has been assigned to the same assignee as the present application, and copending application Ser. No. 07/846,460, entitled METHOD AND SYSTEM FOR RECORDING AND REPORTING A SEQUENTIAL SERIES OF PACING EVENTS, filed Mar. 2, 1992, which application is assigned to the same assignee as the present application.

The use of the temporary memory portion 402 is described above. Basically, the temporary memory portion 402, when used, provides a "safe harbor" wherein a control program can be temporarily held while a new control program is being downloaded to the program memory portion 404.

In some embodiments of the invention, the program memory portion 404 may be further divided into separate program memory portions, with each separate program memory portion including a different control program that may be invoked by the control processor 30 for a specific purpose or function.

Figure 6:
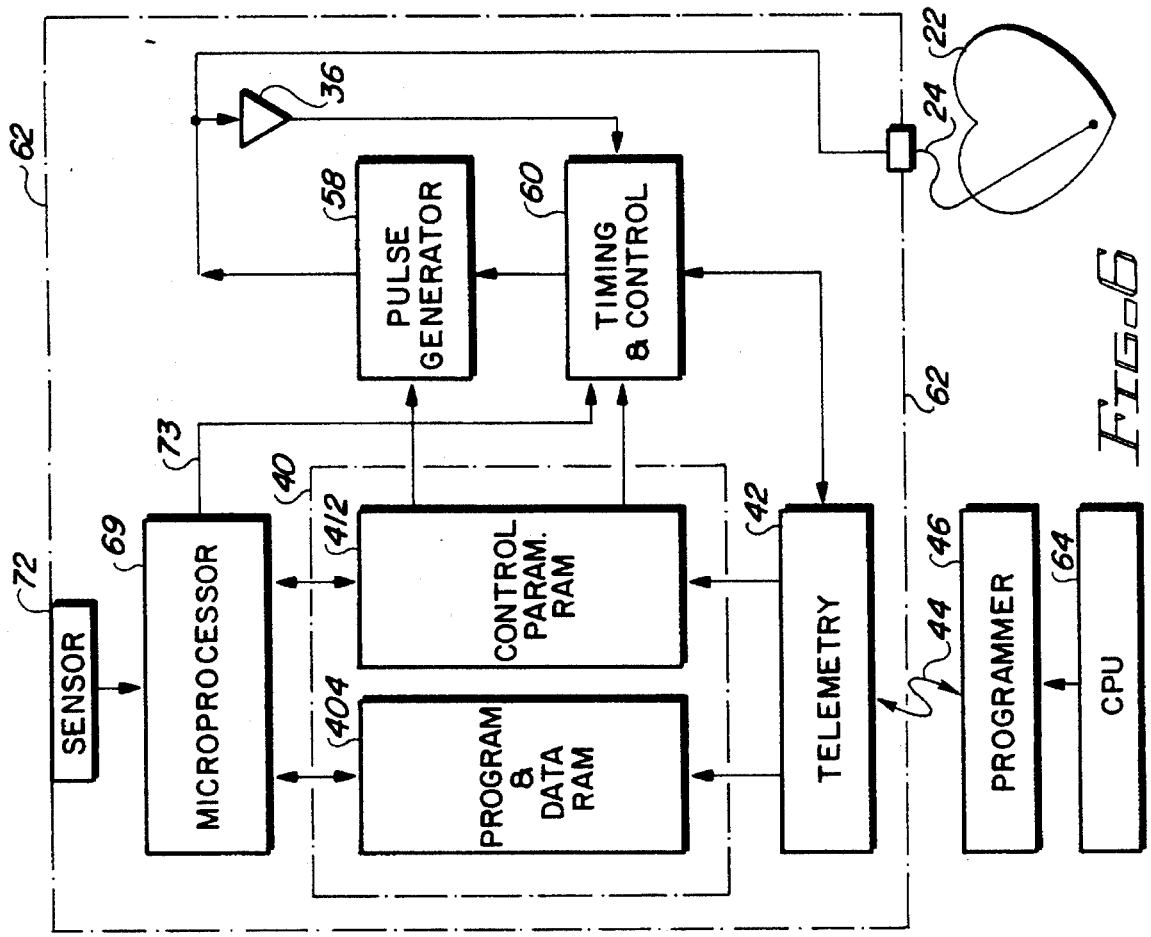
FIG. 6 shows a block diagram of a rate-responsive pacing system made in accordance with the present invention.

Turning next to FIG. 6, there is shown a functional block diagram of a rate-responsive pacing system made in accordance with the present invention. Such rate-responsive pacing system represents one exemplary application of a pacing system that may be noninvasively altered in accordance with the present invention. Like numerals are used to refer to like components in FIG. 6 as are used in FIGS. 1 and 2.

As seen in FIG. 6, the rate-responsive pacing system includes an implantable pacemaker 62 in contact with the patient's heart 22 by way of at least one implantable pacing lead 24. The implantable pacer 62 may be noninvasively contacted by way of the telemetry link 44, established using the external programmer 46. In turn, the external programmer 46 may be coupled to a central processing unit (CPU) 64. The CPU 64, for example, may be used to write, test, revise, and download a desired control program to the external programmer 46, from which location such program is further downloaded to the pacemaker 62.

The implantable rate-responsive pacemaker 62 includes a pulse generator 58 that generates stimulation pulses 59, as controlled by timing and control logic 60, that are directed to the heart 22 over the pacing lead 24. The lead 24 is also connected to a sense amplifier 36. Further included within the pacemaker 62 is a memory 40 that is made up of control parameter RAM 412 and a program RAM 404. The sense amplifier 36 monitors the lead 24 for the occurrence of any electrical signals, picked up within the heart 22, that may evidence natural cardiac activity. If such signals are sensed, they are directed to the timing and control logic 60. The timing and control logic 60 includes a state machine, or equivalent logic, that controls the operation of the pulse generator 58 in accordance with selected control parameters stored in the control parameter RAM 412.

A microprocessor 69 is coupled to the program RAM 404 and the control parameter RAM 412. The microprocessor 69 is also coupled to a physiological sensor 72. The physiological sensor 72 senses a prescribed physiological parameter associated with the patient's physiological need, such as physical activity, or blood oxygen level. A raw sensor signal is generated by the sensor 72 as a function of the physiological parameter that is sensed. The microprocessor 69 processes the raw sensor signal as directed by a control program stored in the program RAM 404 in order to arrive at a sensor-indicated rate (SIR) signal. Typically, such microprocessor 69 converts the raw sensor signal using an appropriate transfer function to the SIR signal, but the SIR signal has certain maximum and minimum values associated therewith. The SIR signal, in turn, is directed to the timing and control logic 60 over signal line 73. The timing and control logic 60, in turn, uses such SIR signal to set the escape interval of the pacemaker when the pacemaker is operating in a rate-responsive mode. This process is more fully described in U.S. Pat. No. 4,940,052.

Referring next to FIG. 7, another block diagram of the rate-responsive pacer 62 of FIG. 6 is shown. FIG. 7 differs from FIG. 6 in that FIG. 6 is a functional block diagram, whereas FIG. 7 is more of a hardware block diagram. However, as can be seen by a comparison of the two figures, many of the components of the two diagrams are the same or similar (and for that reason, identical or similar components share common reference numerals).

As seen in FIG. 7, the pacer 62 includes a conventional pacer hybrid circuit 68 and a microprocessor rate-responsive hybrid circuit 70. Also included in the pacer is a piezoelectric sensor 72 that is connected to the microprocessor hybrid circuit 70. The only electrical connection between the pacer hybrid circuit 68 and the microprocessor hybrid circuit 70 is an I/O bus 74 and power and ground connections (not shown). Included within or connected to the pacer hybrid circuit 68 are conventional pacer components, those shown in FIG. 1, and including a magnetic reed switch 76, a system clock oscillator 78, a telemetry coil 80, and a connector block 82 to which industry-standard atrial and ventricular pacing leads can be connected. A battery 77 is likewise included within the pacer 62.

Figure 9:
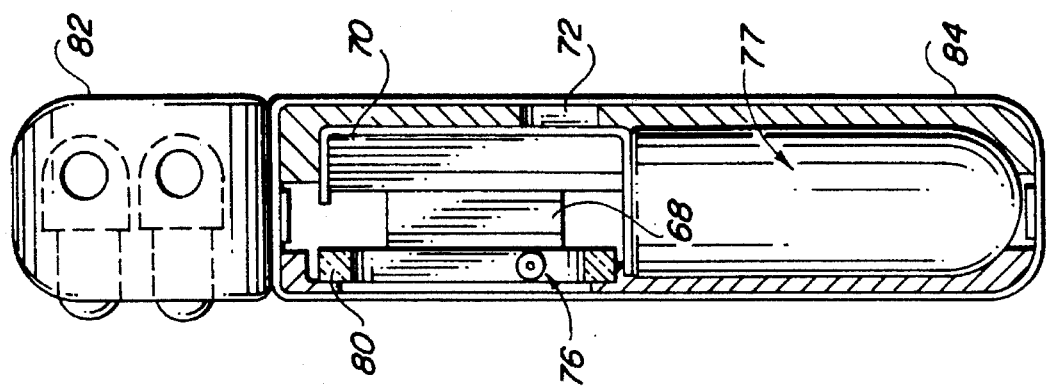
FIGS. 8 and 9 illustrate different cutaway views of the rate-responsive pacer of FIG. 7.
Figure 8:
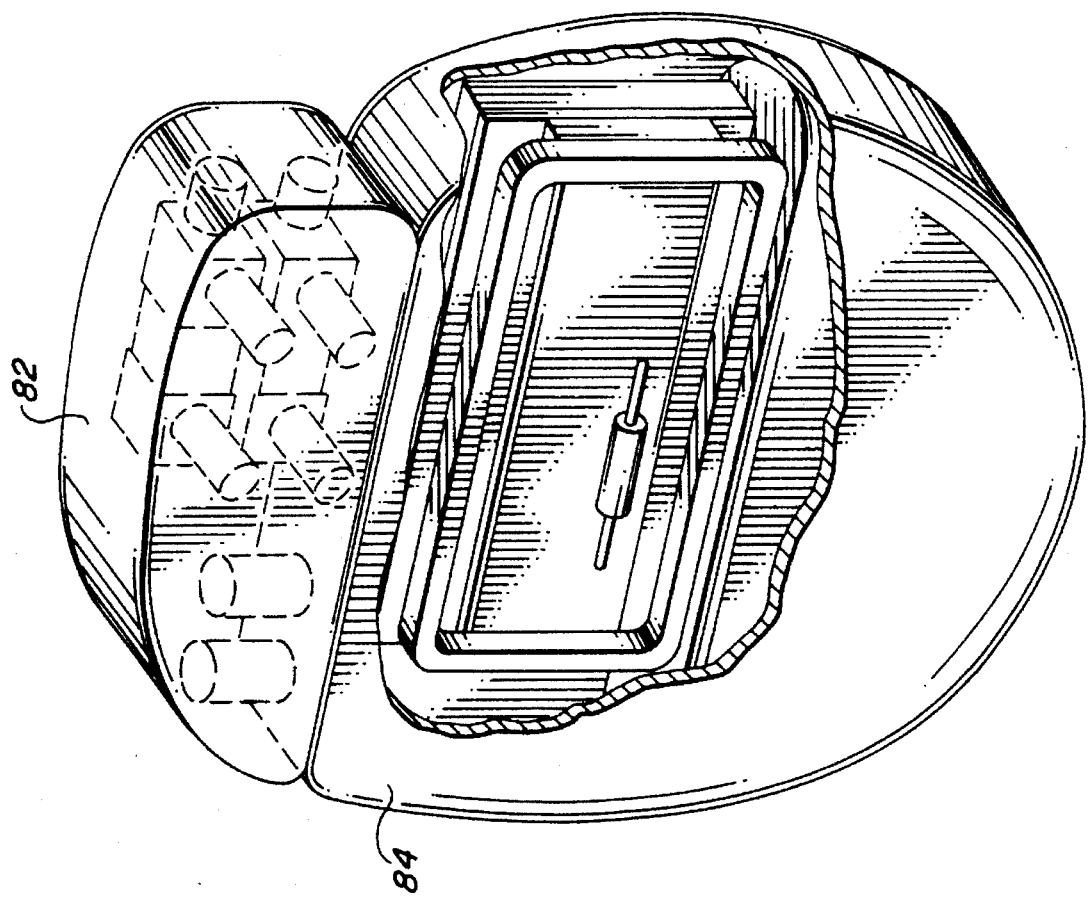

The preferred manner in which the above-enumerated components, as well as the sensor 72 and the microprocessor hybrid circuit 70 are packaged within a suitable enclosure or case 84 is illustrated in the cutaway views of FIGS. 8 and 9. FIG. 8 comprises a perspective cutaway view while FIG. 9 comprises an end cutaway view. As seen in these figures, the pacer hybrid circuit 68 and the microprocessor hybrid circuit 70 are placed side by side above the battery 77. The piezoelectric sensor 72 is bonded between the case 84 and the microprocessor hybrid circuit 70 so as to detect any pressure applied to the case 84 (such as occurs when the patient engages in physical activity).

Referring again to FIG. 7, the microprocessor hybrid circuit 70 includes a microprocessor circuit 86 that is electrically connected to the I/O bus 74. Such I/O bus is realized with a flex circuit. Also included as part of the microprocessor hybrid circuit 70, as shown in FIG. 7, are a random access memory (RAM) 88, read only memory (ROM) 90, a timer circuit 92, control logic 94, a counter 96, a voltage controlled oscillator (VCO) 98, a preamplifier and rectifying circuit 100, a reference voltage circuit 102, and functional AND gate 104. All of these components cooperate to produce a digital signal representative of the energy content of the raw signal obtained from the piezoelectric sensor 72 in a manner the same as, or substantially similar to, that described in U.S. Pat. No. 4,940,053, incorporated herein by reference. The raw signal from the sensor 72 is amplified and rectified and filtered in circuit 100. The resulting analog signal drives VCO 98, the output of which is counted in counter 96 for a prescribed period of time (the sample time), set by timer circuit 92. At the end of the counting period, the final count held in counter 96 is thus representative of the frequency variations of VCO 98, which variations, in turn, are representative of the energy content of the raw sensor signal. Hence, the count held in counter 96 provides a digital signal that represents the energy content of the raw signal. This digital signal can then be transferred to either the microprocessor 86 for further processing, or to RAM 88 for storage, over data/control bus 104. Data/control bus 104 interconnects the counter 96, control logic 94, ROM 90, timer circuit 92, RAM 88 and microprocessor 86.

The case 84 (FIGS. 8 and 9) in which the components as above described are housed is preferably made from titanium coated with a biocompatible insulating material on all but one side. This exposed side functions as a return electrode for any unipolar modes of operation that may be selected.

The battery 77 is a lithium-iodine battery model 8074, manufactured by Wilson Greatbach Company, or equivalent. This battery provides 2.3 ampere hours of usable energy at nominal pacing conditions (dual bipolar operation, 70 ppm, standard parameters, 100% pacing).

The ROM 90 is a 1K×8-bit memory that contains the basic program used to load desired software into the on-board RAM 88. RAM 88 comprises an 8K×8-bit CMOS device that provides the needed storage space for the desired software. The microprocessor 86 is a MC146805 CMOS Static Microprocessor manufactured by Motorola. It is the control center for implementation of the desired software. The software stored in the RAM 88 is utilized by the microprocessor 86 to: (1) perform sensor-data acquisition and to generate the sensor-indicated rate signal from the signal held in counter 96 at the sample time; (2) control the pacer hybrid circuit 68 (for the SENSOR ON Mode); (3) perform data transfers between RAM 88, the control logic 94, the I/O bus 74 (for monitoring and control of the various states of the pacer hybrid circuit 68); (4) compute running averages of the sensor index signal or other calculations needed or desired; and (5) perform whatever other tasks need to be done for a particular application as directed by the controlling software. Inasmuch as a commercially available microprocessor is used for the processor 86, the operation and use of which is well documented in the art, those skilled in the art could readily provide the necessary programs for accomplishing the tasks described herein.

Figure 10:
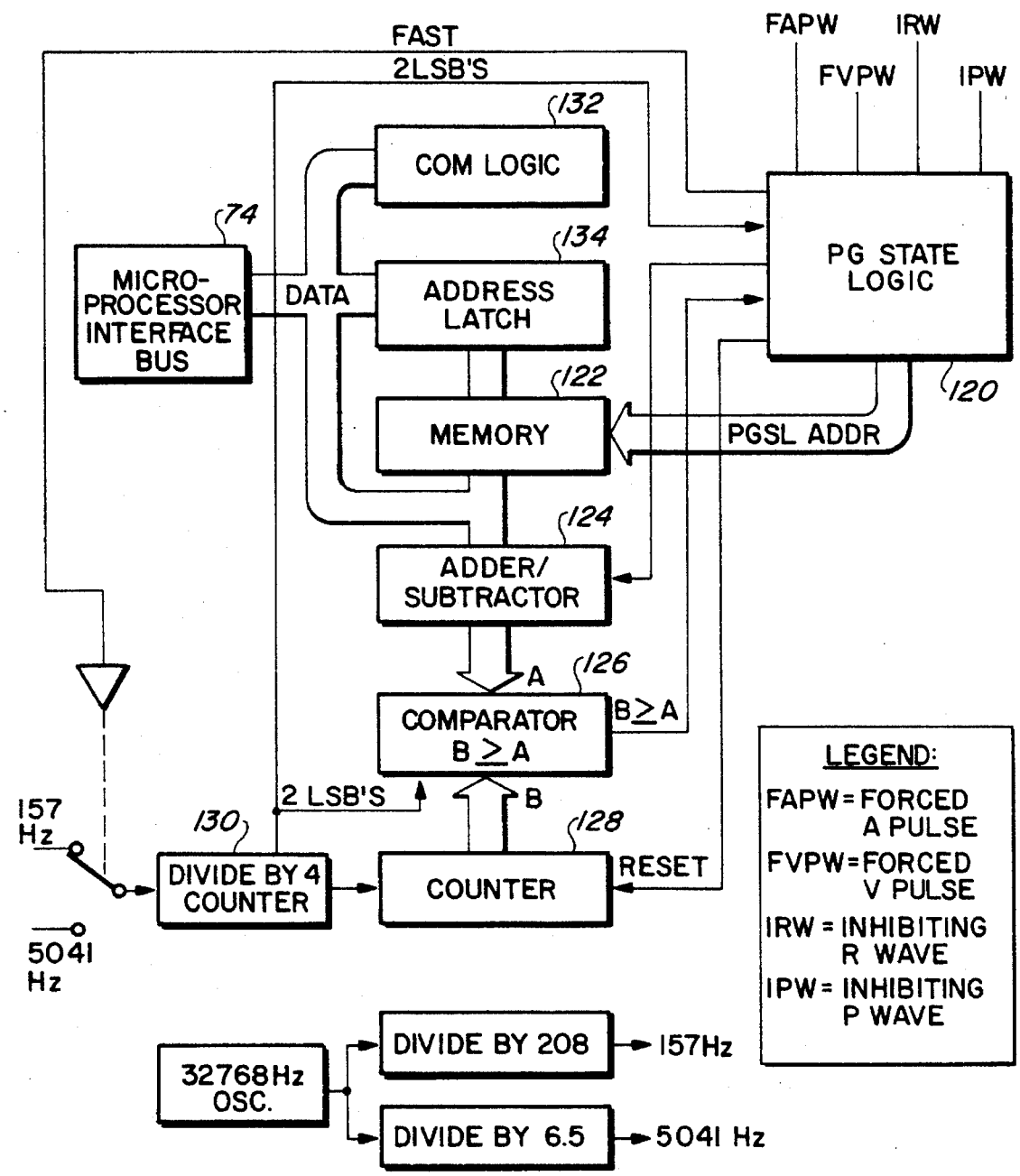
FIG. 10 is a block diagram of selected portions of the conventional pacer hybrid portion of the pacemaker of FIG. 7.

Referring next to FIG. 10, a block diagram of selected portions of the pacer hybrid circuit 68 is shown. The pacer hybrid circuit operates on the state machine principle where all events of the pacer are based on a Pulse Generator (PG) state logic 4-bit register 120. The state of the PG state logic 120 is determined by a state timer and/or sensed cardiac events. As various sensed events occur, and/or as various time intervals expire, the state of the PG state logic 120 thus cycles through different states.

The concept of a state machine as applied to a pacemaker is explained more fully in U.S. Pat. No. 4,712,555, which patent has already been incorporated herein by reference. FIGS. 14A–14C and FIG. 15 of the '555 referenced patent, and accompanying text, illustrate state machine operation. For purposes of the present invention, it suffices to state that each pacing cycle is comprised of a plurality of states, each state initiating a specified time interval (such as a blanking interval, an absolute refractory period, or a V-A delay), some of which intervals can be reset in the event a sensed cardiac event occurs. The occurrence of some states is common to all pacing cycles. The occurrence of other states depend upon the particular programmed mode of operation of the pacer and/or the particular cardiac events that are sensed. Hence, it is a relatively simple matter to define a pacing cycle (and to develop an appropriate sampling signal that occurs every pacing cycle) by monitoring the PG state logic 120. The occurrence of a common state, followed by the occurrence of at least one other state, followed by the reoccurrence of the same common state, thus signals that a cardiac cycle has been completed. Hence, by simply monitoring when one of these common states occurs, such as the V-A delay state (VAD), an indication is provided that a pacing cycle has occurred. The occurrence of a pacing cycle is an important event to note during the operation of the pacemaker 62 because many significant events occur, such as the updating of the SIR signal, once each pacing cycle.

Coupled to the PG state logic 120 is memory circuitry 122. The memory circuitry 122 has prescribed control signals stored therein at specified locations. These control signals are addressed by the state of the state logic 120. These control signals, once addressed by the state logic, may be further processed, such as by adder/subtractor 124 and comparator 126, and related circuitry (such as counter 28, divide circuit 130, and other circuits not shown), in order to bring about a desired event, such as the starting of a prescribed time interval. Once the prescribed event occurs, e.g. as the timing out of a particular time interval, or once a sensed cardiac event occurs, appropriate steering signals are fed back to the PG state logic 120 to cause the next appropriate state of the PG state logic to be entered.

The PG state logic states for the pacer hybrid circuit 68 are summarized in Table 1. The normal sequence for the PG state logic state machine in the absence of P or R waves or noise in any pacing mode is: 0, 1, 5, 4, 6, 2, A, B, 9, 8, C, 0.

TABLE 1

States of PG State Logic

| State | Symbol | Description |
|---|---|---|
| 0 | APW | A Pulse |
| 1 | BLANK | V Sense Input Inhibit (Blank) |
| 2 | AREF | A Refractory |
| 3 | SIPW | Sensed Inhibiting P Wave |
| 4 | AVD | A-V Delay |
| 5 | CROSS | Crosstalk Sense |
| 6 | VPW | V Pulse |
| 7 | SIRW | Sensed Inhibiting R Wave |
| 8 | VAD | V-A Delay |
| 9 | SHORT1 | Shorten A-V Delay 50 msec if IPW during SHORT1 with Physiologic A-V Delay On |
| A | MTR | Maximum Track Rate -- Shorten A-V Delay 25/75 msec and Delay IPW until MTR end if P wave sensed during MTR; 75 msec if Physiologic A-V Delay On |
| B | SHORT2 | Shorten A-V Delay 75 msec if IPW during SHORT2 with Physiologic A-V Delay On. |
| C | RRT | Lengthen V-A interval if at low battery. |
| D | RNOISE | R Noise sensed during VREF or RNOISE. |
| E | LIPW | Latched IPW -- P wave sensed in MTR. |

TABLE 1-continued

States of PG State Logic

| State | Symbol | Description |
|---|---|---|
| F | PNOISE | P Noise sensed during AREF or PNOISE. |
| (none) | VREF | V Refractory, independent 1-bit state machine synchronized to PGSL when AREF starts. |
| (none) | ABSREF | 108 msec Absolute Refractory starts when AREF starts. |

In addition to the PG state logic 120, various communication states can be set by the COM logic 132. COM logic 132 determines the telemetry state of the pacer. The particular sequence of COM states depends on the type of telemetry command (memory, measured data, or interrogate) that is received from the external programmer 46 (FIG. 1). For purposes of the present invention, it is only significant to note that both the memory 122 and COM logic 132, as well as address latch 134, are coupled to the microprocessor interface bus 74. Hence, data can be sent to the microprocessor I/O hybrid circuit 70 from the pacer hybrid circuit 68 (which may include data or information received from the external programmer); or data can be received by the pacer hybrid circuit 68 from the microprocessor hybrid circuit 70 (which may include data or information that is to be sent to the external programmer). The details of the manner in which such data transfers may occur are known to those skilled in the art.

Some of the data that may be sent from the microprocessor hybrid circuit 70 to the pacer hybrid circuit 68 includes the sensor-indicated rate signal sampled at an appropriate (and selectable) sampling interval. This signal can be stored within the memory circuits of the pacer and later retrieved and sent to the external programmer 46, or equivalent device, and displayed in a convenient histogram format.

Figure 11:
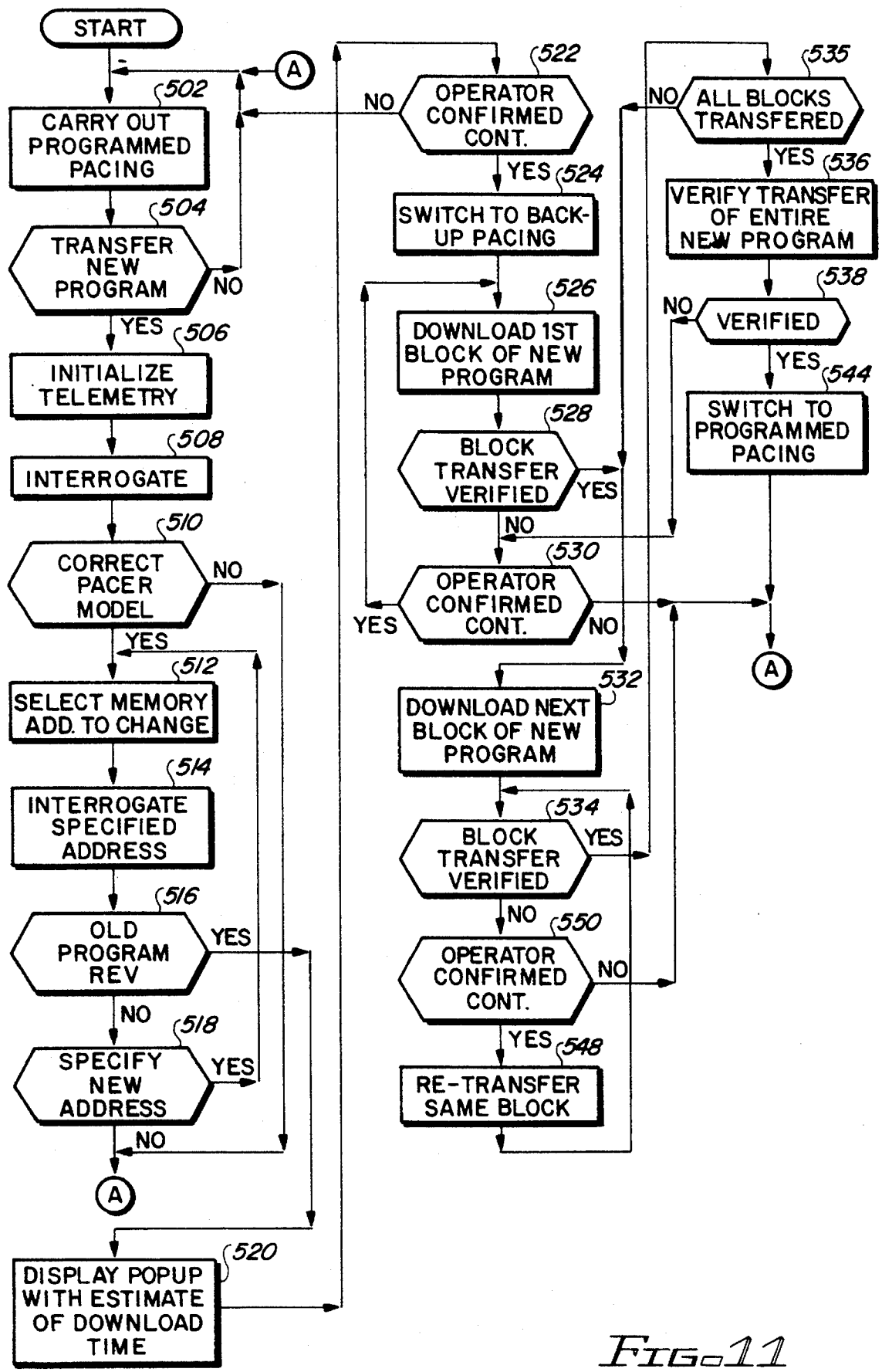
FIG. 11 is a simplified flowchart that depicts the process of downloading a new control program to the memory of the device of FIG. 7.

Referring next to FIG. 11, a simplified flowchart that depicts the process of downloading a new control program to the program memory 404 of the pacemaker 62 of FIGS. 6 and 7 is illustrated. Once the operation of the pacemaker is initiated, the programmed pacing is carried out in accordance with the specified mode of operation, programmed control parameters, and control program stored in the pacer memory, in conventional manner (block 502). As needed, a determination is made as to whether a new software control program is to be downloaded to the control program memory (block 504). If a new program is to be downloaded ("yes" branch of block 504), a telemetry link is initialized (block 506) in conventional manner between the external programmer 46 and the pacemaker 62. Once the telemetry link is thus established, the external programmer performs an initial interrogate operation (block 508) in order to check the contents of the pacer memory 40. Such initial interrogation provides an indication, for example, of the model of the pacemaker that is implanted.

If the interrogation shows that the pacer model is one wherein the control program may not be updated or changed ("no" branch of block 510), then the pacer returns to its programmed operation (block 502), and no further action is taken. If the interrogation (performed at block 508) shows that the pacer model is one wherein the control program may be updated ("yes" branch of block 510), then the operator of the external programmer is prompted to select a memory address that is to be changed (block 512). In some embodiments, this selection may be made automatically by the programmer based on the sensed model of the pacer. The selected (or otherwise determined) memory address is then interrogated (block 514), and a determination is made as to whether such memory address contains an old control program revision (block 516), i.e., an early revision of the control program that has since been updated. If not ("no" branch of block 516), then a new memory address may be specified ("yes" branch of block 518, and block 512), and the process of interrogation at the newly specified memory address repeats (blocks 514, 516). If the specified memory location does contain an old control program ("yes" branch of block 516), then a "popup" display is presented on the programmer screen that provides an estimate of the download time, and the operator is asked to confirm whether or not the download operation is to proceed (block 522).

If the operator elects not to go forward with the download operation ("no" branch of block 522), e.g., if the operator decides that the operation will take too long, then the pacer returns its regularly programmed operation (block 502).

If the operator elects to go forward with the download operation ("yes" branch of block 522), then the programmer sends an appropriate command that causes the pacer to switch to a selected backup pacing mode (block 524). In this instance, where the pacemaker 62 comprises a rate-responsive pacemaker, such backup pacing mode comprises any of the non-rate-responsive pacing modes available using the hybrid pacing chip 68. Typically, the backup pacing mode will be a single-chamber mode, such as VVI (to minimize power consumption); but it could just as easily be a dual-chamber pacing mode, such as DDI, if the patient's condition indicated that such a dual-chamber pacing mode were needed.

Once the backup pacing mode has been established, then a first block of the new control program is downloaded to the specified memory address (block 526). After the first block has been downloaded, its accurate transfer is verified (block 528). If the transfer is not verified ("no" branch of block 528), i.e., if a determination is made that an error occurred, or only part of the block was transferred, etc., and if a determination is made that the downloading process should continue (block 530), then the first block is again downloaded (block 526). This process continues until the first block is successfully downloaded, or until a determination is made by the operator (block 530) to cease the downloading process.

Once the accurate transfer of the first block of the new control program is verified ("yes" branch of block 528), then the next block of the new control program is downloaded in like manner (block 532). After transfer of the next block, a determination is made as to whether it was transferred correctly (block 534). If not ("no" branch of block 534), and if a determination is made that the downloading process should continue (block 550), then this same block is downloaded again (block 548). This process continues until the block being downloaded is successfully downloaded, or until a determination is made by the operator (block 550) to cease the downloading process.

If the downloading of the block is verified ("yes" branch of block 534), then a determination is made as to whether all the blocks of the new control program have been downloaded (block 535). If not ("no" branch of block 535), then the new block of the new control program is downloaded, and the process repeats (blocks 532, 534, 535, 550 and 548). If yes ("yes" branch of block 535), then the transfer of the entire control program is next verified (block 536). If successful verification is made of the entire new control program ("yes" branch of block 538), then the program control of the pacemaker is switched back to programmed pacing as controlled by the new control program (block 544). Thereafter, the programmed pacing is carried out by the new control program (block 502).

Should the transfer of the entire new control program not be verified ("no" branch of block 538), and should a decision be made by the operator to continue downloading of the program (block 530), then the downloading operation returns to the first block of the new control program, and the process repeats (blocks 526–538).

It is to be understood that in some embodiments of the invention, the external programmer 46 may display a bar graph that graphically depicts the percent of the downloading operation that has been completed, as well as an estimate of the time remaining to complete the transfer. Such displays are common in the industry when used with the downloading of data from one computer to another, especially when such downloading is performed via a modem through an established telecommunications link, e.g., through a telephone line. Advantageously, the same procedures and protocol used to perform such data transfers over a telephone line can be used, with some modifications, in order to download the new control program to the pacemaker.

As described above, it is thus seen that the invention provides a method whereby an external device can communicate with an implanted pacemaker in order to change the contents of the pacemaker memory. Mechanisms are used in such method to safeguard the integrity of the pacemaker operation as well as the safety of the patient. The programmer may advantageously be an existing programmer, such as the APS-II programmer manufactured by Siemens Pacesetter, Inc. of Sylmar, Calif. The APS-II programmer is described, e.g., in U.S. Pat. No. 4,809,697.

The new program to be transferred to the pacemaker may be contained in a ROM memory located in the programmer. In this respect, it is noted that the APS-II programmer described in the '697 patent, for example, allows a removable program cartridge, containing a ROM, to be installed on the main printed wiring board of the APS-II programmer. Thus, it is a relatively simple task to load new ROM into the programmer. Advantageously, however, only authorized personnel are given access to a program cartridge that would permit downloading of a new control program. Thus, an additional measure of security is provided because the correct program cartridge functions as a "key" that is only in the possession of authorized personnel.

Further, it is noted that the new control program to be transferred to the pacemaker may be transferred to the programmer from an external computer, e.g., the CPU 64 (FIG. 6). The APS-II programmer, or equivalent programmer, formats the new control program in small packets of data or code which are transmitted to the pacemaker through the noninvasive telemetry link established between the programmer and pacemaker in conventional manner. The pacemaker, upon reception of the packet of data/code, stores the data/code in its memory and responds to the programmer by transmitting the data back to the programmer for verification against the originally transmitted data/code. When all data/code packets are transmitted to the pacemaker and each packet received by the pacemaker returns an acceptable response, the programmer reads the entire program from the pacemaker to ensure data integrity. Only then does the programmer issue a command to the pacemaker to begin execution of the newly stored control program.

In one embodiment, the pacemaker memory 40 includes 8192 bytes of storage, used for the storage of both the control program and data. The typical allowance for the control program storage is approximately 3000 bytes. The remainder of the memory is devoted to Event Records (4096 bytes), Event Histogram (192 bytes), SIR Histogram (92 bytes), sensor parameter storage (32 bytes), and general data storage.

As indicated above, heretofore the design of the memory access system for a pacemaker has allowed the programmer to write to only the sensor or control parameter storage area of the pacemaker memory. Such limited access afforded the security of avoiding inadvertent changes to the program. Any area of the program could be read by field clinical engineers for system diagnostic purposes, i.e., to manually verify that the control program and/or control parameters had been correctly loaded into the pacemaker. Such "read only" capability is referred to in the APS-II programmer as the "Engineering Test Page."

The present invention advantageously maintains the security of normal operation, but allows changes to be made to the program under a tightly controlled situation. An interlock scheme is used, like a password, that allows changes to be made to the control program only by authorized individuals. Such access is not allowed through the Engineering Test Page, but is an option to the Engineering Test Page. To use the option, a predetermined sequence of passwords must be entered into the programmer at the right time after the telemetry link has been established. In some embodiments, such sequence of passwords must be entered without prompting. Because the passwords themselves, plus the password entry sequence, are known only to authorized individuals, a high level of security is thus maintained. In other embodiments, the option is listed as an option of the Engineering Test Page screen display Applications of the present invention—being able to noninvasively upgrade the pacemaker control program—are numerous and varied. For example, features may be added to the existing pacemaker by loading a new control program that includes the new features. For instance, a rate-responsive pacemaker may be upgraded to include a new feature, such as rate hysteresis, or to respond to a new type of sensor, or to process the existing raw sensor signal in a different manner. Note that rate hysteresis is an approach that uses many of the same principals used in rate-responsive pacing to adjust the pacemaker timing, but in such a way that the patient's intrinsic rate, though lower than the paced rate, can be allowed to take precedence to achieve maximum hemodynamic benefit. Rate hysteresis is more fully described in U.S. Pat. No. 5,374,281, granted Dec. 20, 1994, entitled HSYTERESIS IN A RATE-RESPONSIVE PACEMAKER, which is incorporated herein by reference.

A further application for the present invention is to alter the pacemaker control program slightly for the purpose of adjusting the duty cycle of the microprocessor. Such change achieves economies in battery current usage, thus extending the usable life of the pacemaker. Hence, by simply upgrading the control program of an existing pacemaker, the pacemaker life may be extended.

Similarly, the present invention facilitates the loading of temporary programs that remain effective only in the presence of a magnet. Such temporary programs are useful for production tests where there is a need to test a certain feature without having a permanent effect of the normal pacemaker function or memory requirements. Such temporary programs are also useful to a physician, after implant, to allow certain diagnostic tests to be performed on the patient, only when the magnet is present, that could not otherwise be performed. Once the magnet is removed, the temporary programs are no longer be effective.

While the invention herein disclosed has been described by means of specific embodiments and applications thereof, numerous modifications and variations could be made thereto by those skilled in the art without departing from the scope of the invention set forth in the claims.

What is claimed is:

1. A system for nonivasively altering the function of an implantable pacemaker by an external programmer, comprising:

an implantable pacemaker comprising:
 pulse generator means for providing stimulation pulses,
 control means for controlling the pulse generator means in accordance with a basic operating mode,
 a memory device,
 processor means for conditioning the operation of the pacemaker in accordance with a first control program stored in the memory device, said first control program comprising program instructions for controlling the processor means, and control parameters for specifying at least one function carried out by said implantable pacemaker, and
 telemetry means coupled to the processor means and memory device for transferring program instructions and control parameters to the memory device from the external programmer;

an external programmer comprising:
 means for establishing a telecommunicative channel between the telemetry means of said implantable pacemaker and said external programmer through which selected control parameters associated with said first control program may be selectively changed;
 means for verifying at the external programmer the type of implantable pacemaker with which the telecommunicative channel has been established, and for verifying that the first control program stored in the memory device of said implantable pacemaker is one that is to be replaced; and
 means for downloading a second control program from said external programmer to the memory device of said implantable pacemaker while the pulse generator means of said implantable pacemaker continues to operate in said basic operating mode as controlled by said control means, said second control program comprising new program instructions and control parameters for controlling the processor means so that an altered function is carried out by said implantable pacemaker, the second control program replacing said first control program, whereby at least one function carried out by said implantable pacemaker may be noninvasively altered during the same time that said implantable pacemaker continues to operate in said basic operating mode.

2. A system, as set forth in claim 1, wherein said means for downloading further comprises means for writing the second control program to a memory location within the memory device where the first control program is stored, thereby overriding the first control program with the second control program.

3. A system, as set forth in claim 1, wherein said means for downloading also comprises transfer verification means for verifying that the second control program has been accurately transferred to and stored within the memory device of the implantable pacemaker.

4. A system, as set forth in claim 3, wherein said transfer verification means comprises means for dividing and forming the second control program into blocks of new program instructions and control parameters, each block thus formed thereby comprising a portion of the second control program, means for transferring said blocks to the memory device of the implantable pacemaker one block at a time, and means for verifying the accurate transfer of each block prior to beginning the transfer of a next block.

5. A system, as set forth in claim 1, wherein said means for downloading comprises means for writing the second control program to a memory location within the memory device where the first control program is stored, thereby overriding the first control program with the second control program, and wherein said memory device includes a temporary memory location, and further wherein said means for downloading also comprises means for copying and storing the first control program to the temporary memory location within said memory device prior to overriding it with the second control program, and for maintaining the copy of the first control program in the temporary memory location until an accurate transfer of the second control program to the pacemaker memory device has been confirmed.

6. A system, as set forth in claim 1, wherein said implantable pacemaker, further comprises:

a first pacing chip comprising
said pulse generator means,
a basic memory element into which a set of control parameters that control the operation of the first pacing chip in accordance with the basic operating mode may be programmably stored, and
said control means, wherein said control means includes means for controlling the pulse generator means in accordance with the set of control parameters stored in the basic memory element; and wherein the processor means includes a second pacing chip comprising
a microprocessor, and
associated memory means coupled to said microprocessor for storing said first and second control programs.

7. A system, as set forth in claim 6, wherein said means for downloading comprises:

means for programming the set of control parameters into the basic memory element of the first pacing chip, said set of control parameters defining the basic operating mode of said pulse generating means of said first pacing chip, whereby the basic operating mode may be followed by said pulse generator means without reference to said first control program;

means for writing the second control program into the associated memory means of the second pacing chip while the pulse generator means is controlled by the set of control parameters stored in the basic memory element of the first pacing chip; and means for modifying the control means of the first pacing chip after the second control program has been written to the associated memory means of the second pacing chip to provide the implantable pacemaker with the altered function defined by the new program instructions and control parameters of the second control program.

8. A system for noninvasively altering the function of an implantable pacemaker by an external programmer, comprising:

an implantable pacemaker comprising:
pulse generator means for providing stimulation pulses,
control means for controlling the pulse generator means in accordance with a basic operating mode,
a memory device,
processor means for conditioning the operation of the pacemaker in accordance with a first control program stored in the memory device, said first control program comprising program instructions for controlling the processor means, and control parameters for specifying at least one function carried out by said implantable pacemaker, and
telemetry means coupled to the processor means and memory device for transferring program instructions and control parameters to the memory device from an external location;

an external programmer having means for establishing a telecommunicative channel between the telemetry means of said implantable pacemaker and said external programmer through which selected control parameters associated with said first control program may be selectively changed;

means for verifying at the external programmer that the first control program stored in the memory device of said implantable pacemaker is one that is to be replaced; and means for downloading a second control program from said external programmer to the memory device of said implantable pacemaker through said telecommunicative channel, said second control program being stored in said memory device so as to replace said first control program.

9. A system, as set forth in claim 8, wherein said means for downloading also comprises transfer verification means for verifying that the second control program has been accurately transferred to and stored within the memory device of the implantable pacemaker.

10. A system, as set forth in claim 9, wherein said memory device includes a temporary memory location, and wherein said means for downloading comprises means for copying and storing the first control program to the temporary memory location within said memory device prior to downloading the second control program, and for maintaining the copy of the first control program in the temporary memory location until an accurate transfer of the second control program to the pacemaker memory device has been verified.

11. A system, as set forth in claim 8, wherein said implantable pacemaker, further comprises:

a first pacing chip comprising
said pulse generator means,
a basic memory element into which a set of control parameters that control the operation of the first pacing chip may be programmably stored, and
said control means, wherein said control means includes means for controlling the pulse generator in accordance with the set of control parameters stored in the basic memory element; and wherein the processor means includes a second pacing chip comprising
a microprocessor, and
associated memory means coupled to said microprocessor for storing said first and second control programs.

12. A system, as set forth in claim 11, wherein said means for downloading comprises:

means for programming a set of control parameters in the basic memory element of the first pacing chip, said set of control parameters defining the basic operating mode for said pulse generator of said first pacing chip, whereby the basic operating mode is followed by said pulse generator without reference to said first control program;

means for writing the second control program into the associated memory means of the second pacing chip while the pulse generator is controlled by the set of control parameters stored in the basic memory element of the first pacing chip; and means for modifying the control means of the first pacing chip after the second control program has been written to the associated memory means of the second pacing chip.

13. A method for noninvasively altering the function of an implantable pacemaker while said pacemaker continues to perform a basic pacing function of providing stimulation pulses to a patient's heart in a prescribed manner, said implantable pacemaker having a processor, a memory, means for establishing a telecommunicative channel with said pacemaker, and control means for controlling the functions carried out by said pacemaker in accordance with an existing control program and control parameters stored in the memory included within said pacemaker, said control program and control parameters being downloadable through said telecommunicative channel for storage in said memory, said method comprising the steps of:

(a) establishing a telecommunicative channel with said implantable pacemaker from a non-implanted, remote location;

(b) verifying through said telecommunicative channel that the existing control program is one that is to be replaced;

(c) controlling said implantable pacemaker through said established telecommunicative channel to provide stimulation pulses in a prescribed manner without relying on the existing control program stored in said memory;

(d) downloading a new control program through said established telecommunicative channel from said remote location and storing said new control program in said memory of said implantable pacemaker so as to replace said existing control program, said new control program being adapted to alter the functions the implantable pacemaker carries out; said implantable pacemaker continuing to provide stimulation pulses to the patient's heart in the prescribed manner while the new control program is being downloaded and stored in said memory;

(e) controlling said implantable pacemaker through said established telecommunicative channel to execute new pacing functions in accordance with the new control program downloaded to and stored in said memory.

14. A method, as set forth in claim 13, wherein step (d) comprises transmitting the new control program into blocks, where a block comprises a portion of the new control program, and transmitting the new control program one block at a time through said telecommunicative channel, and verifying that each block has been transmitted correctly before transmitting another block.

15. A method, as set forth in claim 14, wherein step (d) further comprises verifying that the new control program has been downloaded correctly after all of the blocks have been transmitted.

16. A method, as set forth in claim 13, wherein step (d) comprises displaying the status of the downloading of the new control program at the remote location as downloading takes place.

17. A method, as set forth in claim 13, wherein said implantable pacemaker comprises a rate-responsive that provides rate-responsive functions in accordance with the control program stored in its memory, and wherein said method further comprises using the new control program downloaded to the memory of said implantable pacemaker to alter the rate-responsive functions of said rate-responsive pacemaker.

18. A method, as set forth in claim 13, wherein the implantable pacemaker includes a battery, and wherein said method further comprises using the new control program to alter a basic duty cycle associated with the processor of said implantable pacemaker so as to conserve energy, thereby extending the battery life of the battery included within said implantable pacemaker.

19. A method, as set forth in claim 13, wherein the memory of the implanted pacemaker is divided into at least two memory portions, with the existing control program being stored in a first one of said at least two memory portions, and wherein step (d) of downloading the new control program through said established telecommunicative channel comprises:

downloading the new control program to a second one of said at least two memory portions, whereby, after the new control program has been downloaded, both said existing and new control programs are stored respectively in said first and second memory portions; and selecting one of the first or second memory portions as the source of a control program that controls the functions of the implantable pacemaker.

20. A method, as set forth in claim 19, wherein step (d) further comprises:

selecting the first memory portion having the existing control program stored therein as the source of the control program that controls the functions of the implantable pacemaker;

downloading the new control program to the second memory portion while the control program stored in the first memory portion continues to control the functions of the implantable pacemaker;

verifying that the new control program has been successfully downloaded into the second memory portion; and then selecting the second memory portion having the new control program stored therein as the source of the control program that controls the functions of the implantable pacemaker.

21. A method, as set forth in claim 13, wherein the memory of said implantable pacemaker includes a temporary memory location, and wherein step (d) comprises transferring the existing control program to the temporary memory location before downloading the new control program.

22. A method, as set forth in claim 21, further comprising verifying that the new control program has been transferred completely and correctly to the memory of the implantable pacemaker, and transferring the existing control program from said temporary memory location back to its original memory location in the event that the downloading of the new control program is not completed nor verified.

23. A pacing system comprising:

an implantable pacemaker having pulse generator means for generating stimulation pulses and delivering said stimulation pulses to a patient's heart, a memory wherein a control program may be stored, telemetry means for transferring control programs to the memory from an external location, and control means for controlling the pulse generator means in accordance with a prescribed mode of operation, said prescribed mode of operation being dependent at least in part upon the control program stored in the memory included within said implantable pacemaker;

said control program having a first portion for controlling operation of the pulse generator means when operating in a rate-responsive mode, and a second portion for controlling operation of the pulse generator means when operating in a non-rate-responsive mode;

an external programmer having means for establishing a telemetry link with the telemetry means of said implantable pacemaker;

verification means at the external programmer for verifying through the telemetry link which of a plurality of control programs are stored in the memory of the implantable pacemaker; and reprogramming means at the external programmer and operable through said telemetry link for noninvasively altering a selected one of said first portion or said second portion of said control program stored in the memory of said implantable pacemaker.

24. A system for noninvasively altering the function of an implantable medical device by an external programmer, comprising:

an implantable medical device comprising:
first means for providing a specified medical function;
a memory device;
processor means for controlling the operation of the first means of the implantable medical device in accordance with a first control program stored in the memory device; and
telemetry means for receiving externally generated signals;

an external programmer having means for establishing a communication link with the telemetry means of said implantable device;

verification means at the external programmer for verifying through the communication link which of a plurality of control programs are stored in the memory of the implantable pacemaker;

means for downloading a second control program from said external programmer through said communication link and storing said second control program within the memory device of said medical device, said downloading means storing said second control program in a memory location of said memory device not occupied by said first control program; and second means, coupled to said telemetry means, for controlling the operation of the first means of the implantable medical device in accordance with said second control program whenever a prescribed externally generated signal is received through said telemetry means.

25. A system, as set forth in claim 24, further comprising means, coupled to said telemetry means, for deactivating said first control program whenever a particular type of externally generated signal is received through said telemetry means.

26. A system, as set forth in claim 24, further comprising means, coupled to said telemetry means, for removing said second control program from the memory device whenever said telemetry means does not receive a particular type of externally generated signal through said telemetry means.

27. A system, as set forth in claim 24, wherein the specified medical function provided by said first means of said implantable medical device comprises detecting cardiac electrical activity.

28. A system, as set forth in claim 24, wherein the specified medical function provided by said first means of said implantable medical device comprises stimulating the heart.

29. A system, as set forth in claim 24, wherein said telemetry means of said implantable medical device comprises means for receiving a magnetic signal.

30. A system, as set forth in claim 24, wherein said telemetry means of said implantable medical device further comprises means for receiving a telemetry signal.

* * * * *

UNITED STATES PATENT AND TRADEMARK OFFICE
CERTIFICATE OF CORRECTION

PATENT NO. : 5,456,692

DATED : October 10, 1995

INVENTOR(S) : Robert E. Smith, Jr.; Jeffery D. Snell

It is certified that error appears in the above-indentified patent and that said Letters Patent is hereby corrected as shown below:

In col. 15, line 36, after "components," insert --such as--.

In col. 25, line 57, delete "transmitting" and substitute therefor --dividing--.

In col. 26, line 5, after "rate-responsive" insert --pacemaker--.

Signed and Sealed this

Twenty-third Day of April, 1996

Attest:

BRUCE LEHMAN

*Attesting Officer*   *Commissioner of Patents and Trademarks*